United States Patent
Morrison et al.

(10) Patent No.: US 11,427,873 B2
(45) Date of Patent: Aug. 30, 2022

(54) METHODS AND SYSTEMS FOR ASSESSING PROLIFERATIVE POTENTIAL AND RESISTANCE TO IMMUNE CHECKPOINT BLOCKADE

(71) Applicant: OMNISEQ, INC., Buffalo, NY (US)

(72) Inventors: Carl Morrison, Fredonia, NY (US); Sarabjot Pabla, Buffalo, NY (US); Jeffrey Conroy, Williamsville, NY (US); Sean Glenn, East Amherst, NY (US)

(73) Assignee: OmniSeq, Inc., Buffalo, NY (US)

( * ) Notice: Subject to any disclaimer, the term of this patent is extended or adjusted under 35 U.S.C. 154(b) by 121 days.

(21) Appl. No.: 16/537,069

(22) Filed: Aug. 9, 2019

(65) Prior Publication Data

US 2020/0048717 A1   Feb. 13, 2020

Related U.S. Application Data

(60) Provisional application No. 62/717,379, filed on Aug. 10, 2018.

(51) Int. Cl.
 *C12Q 1/68* (2018.01)
 *C12Q 1/6886* (2018.01)
 *G01N 33/574* (2006.01)

(52) U.S. Cl.
 CPC ..... *C12Q 1/6886* (2013.01); *G01N 33/57492* (2013.01); *C12Q 2600/106* (2013.01); *C12Q 2600/158* (2013.01)

(58) Field of Classification Search
 None
 See application file for complete search history.

(56) References Cited

U.S. PATENT DOCUMENTS

| | | | |
|---|---|---|---|
| 10,934,595 B2 * | 3/2021 | Faruki | A61P 35/00 |
| 2012/0245235 A1 * | 9/2012 | Rhodes | C12Q 1/6886 514/789 |
| 2015/0247208 A1 * | 9/2015 | Stone | C12Q 1/6886 506/2 |
| 2017/0115291 A1 * | 4/2017 | Wong | G01N 33/5011 |
| 2019/0144942 A1 * | 5/2019 | Shalek | A61K 35/15 424/93.7 |
| 2019/0360053 A1 * | 11/2019 | Mongan | C12Q 1/6886 |
| 2021/0166790 A1 * | 6/2021 | Cowens | G01N 33/57438 |

FOREIGN PATENT DOCUMENTS

| | | |
|---|---|---|
| WO | 2015116868 A2 | 6/2015 |
| WO | 2017042394 A1 | 3/2017 |
| WO | 2018183921 A1 | 10/2018 |

OTHER PUBLICATIONS

Kamphorst et al. Proliferation of PD-1+ CD8 T cells in peripheral blood after PD-1-targeted therapy in lung cancer patients. PNAS; 2017; 114; 19: 4993-4998. (Year: 2017).*
Carosella et al. A Systematic Review of Immunotherapy in Urologic Cancer: Evolving Roles for Targeting of CTLA-4, PD-1/PD-L1, and HLA-G (Review). European Association of Urology; 2015; 68; 267-279 (Year: 2015).*
Wang et al. Biological and Clinical Significance of MAD2L1 and BUB1, Genes Frequently Appearing in Expression Signatures for Breast Cancer Prognosis. PLOS ONE; 2015; 10(8):e0136246: p. 1-16. (Year: 2015).*
Cristescu et al. Pan-tumor genomic biomarkers for PD-1 checkpoint blockade-based immunotherapy. Science; Oct. 2018; 362; 197: p. 1-12. (Year: 2018).*
Zhang and Houghton. Good cops turn bad: The contribution of neutrophils to immune-checkpoint inhibitor treatment failures in cancer. Pharmacology & Therapeutics; 2021; 217; 107662: p. 1-8. (Review) (Year: 2021).*
Kamphorst et al. PNAS; 2017; 114; 19: 4993-4998. (Year: 2017).*
Carosella et al. European Association of Urology; 2015; 68; 267-279 . (Year: 2015).*
Wang et al. PLOS ONE; 2015; 10(8):e0136246: p. 1-16. (Year: 2015).*
Vanpouille-Box, C. et al. Trial watch: Immune checkpoint blockers for cancer therapy. Oncoimmunology 6, e1373237 (2017).
Borghaei, H. et al. Nivolumab versus Docetaxel in Advanced Nonsquamous Non Small-Cell Lung Cancer. N. Engl. J. Med. 373, 1627-1639 (2015).
Garon, E. B. et al. Pembrolizumab for the Treatment of Non Small-Cell Lung Cancer. N. Engl. J. Med. 372, 2018 2028 (2015).
Fehrenbacher, L. et al. Atezolizumab versus docetaxel for patients with previously treated non-small-cell lung cancer (POPLAR): a multicentre, open-label, phase 2 randomised controlled trial. Lancet 387, 1837-1846 (2016).
Andrews, A. Treating with Checkpoint Inhibitors—Figure $1 Million per Patient. Am. Heal. Drug Benefits 8, 9 (2015).
Galluzzi, L., Chan, T. A., Kroemer, G., Wolchok, J. D. & Lopez-Soto, A. The hallmarks of successful anticancer immunotherapy. Sci. Transl. Med. in press (2018).
Morrison, C. et al. Predicting response to checkpoint inhibitors in melanoma beyond PD-L1 and mutational burden. J. Immunother. Cancer 6, 32 (2018).

(Continued)

*Primary Examiner* — Jeanine A Goldberg
*Assistant Examiner* — Wahwah T Johnson
(74) *Attorney, Agent, or Firm* — Bond, Schoeneck & King, PLLC

(57) ABSTRACT

A method for characterizing tumor response to immune checkpoint blockade therapy, comprising: (i) obtaining tissue from the tumor; (ii) measuring, using the tissue, expression of one or more cell proliferation gene markers; (iii) determining, based on the measured expression of the one or more cell proliferation gene markers, a proliferation profile of the tumor; (iv) predicting, based on the determined proliferation profile, response of the tumor to immune checkpoint blockade therapy; and (v) determining, by a physician using the predicted response of the tumor to immune checkpoint blockade therapy, a therapy for the tumor.

3 Claims, 23 Drawing Sheets

(56) References Cited

OTHER PUBLICATIONS

Nishino, M., Ramaiya, N. H., Hatabu, H. & Hodi, F. S. Monitoring immune-checkpoint blockade: response evaluation and biomarker development. 4 2 3 Nat. Rev. Clin. Oncol. 14, 655-668 (2017).
Rizvi, N. A. et al. Mutational landscape determines sensitivity to PD-1 blockade in non-small cell lung cancer. Science (80-. ). 348, 124-128(2015).
First Comprehensive Companion Diagnostic OK'd. Cancer Discov. 8, OF4-OF4 (2018).
Sul, J. et al. FDA Approval Summary: Pembrolizumab for the Treatment of Patients With Metastatic Non-Small Cell Lung Cancer Whose Tumors Express Programmed Death-Ligand 1. Oncologist 21, 643-650 (2016).
Hellmann, M. D. et al. Tumor Mutational Burden and Efficacy of Nivolumab Monotherapy and in Combination with Ipilimumab in Small-Cell Lung Cancer. Cancer Cell 33, 853-861.e4 (2018).
Büttner, R. et al. Programmed Death-Ligand 1 Immunohistochemistry Testing: A Review of Analytical Assays and Clinical Implementation in Non Small-Cell Lung Cancer. J. Clin. Oncol. 35, 3867-3876 (2017).
Paluch, B. E. et al. Robust detection of immune transcripts in FFPE samples using targeted RNA sequencing. Oncotarget 8, 3197-3205 (2017).
Conroy, J. M. et al. Analytical Validation of a Next-Generation Sequencing Assay to Monitor Immune Responses in Solid Tumors. J. Mol. Diagnostics 20, 95-109 (2018).
Chaudhary, R. et al. Estimating tumor mutation burden using next-generation sequencing assay. J. Clin. Oncol. 35, e14529-e14529 (2017).
Kriegsmann, M. & Warth, A. What is better/reliable, mitosis counting or Ki67/MIB1 staining? Transl. Lung Cancer Res. 5, 543-546 (2016).
Alexandrov, L. B. et al. Signatures of mutational processes in human cancer. Nature 500, 415-21 (2013).
Tomasetti, C. & Vogelstein, B. Variation in cancer risk among tissues can be explained by the No. of stem cell divisions. Science (80-. ) 347, 78-81 (2015).
McGranahan, N. & Swanton, C. Clonal Heterogeneity and Tumor Evolution: Past, Present, and the Future. Cell 168, 613-628 (2017).
Andor, N. et al. Pan-cancer analysis of the extent and consequences of intratumor heterogeneity. Nat. Med. 22, 105-113 (2016).
Hellmann, M. D. D. et al. Nivolumab plus Ipilimumab in Lung Cancer with a High Tumor Mutational Burden. N. Engl. J. Med. 378, 2093 2104 (2018).
Shi, W. et al. Expression of MTA2 and Ki-67 in hepatocellular carcinoma and their correlation with prognosis. Int. J. Clin. Exp. Pathol. 8, 13083-9 (2015).
Pan, H. et al. 20-Year Risks of Breast-Cancer Recurrence after Stopping Endocrine Therapy at 5 Years. N. Engl. J. Med. 377, 1836-1846 (2017).
Briest, F. et al. Immunohistochemical Study of Mitosis-regulatory Proteins in Gastroenteropancreatic Neuroendocrine Neoplasms. Anticancer Res. 38, 3863-3870 (2018).
Jakobsen, J. N. & Sørensen, J. B. Clinical impact of ki-67 labeling index in non-small cell lung cancer. Lung Cancer 79, 1-7 (2013).
Ramaker, R. C. et al. RNA sequencing-based cell proliferation analysis across 19 cancers odentifies a subset of proliferation-informative cancers with a common survival signature. Oncotarget 8, 38668-38681 (2017).
Wennerberg, E. et al. Immune recognition of irradiated cancer cells. Immunol. Rev. 280, 220-230 (2017).
Vitale, I. et al. Illicit survival of cancer cells during polyploidization and depolyploidization.Cell Death Differ. 18, 1403-13 (2011).
Baughn, L. B. et al. A Novel Orally Active Small Molecule Potently Induces G 1 Arrest in Primary Myeloma Cells and Prevents Tumor Growth by Specific Inhibition of Cyclin-Dependent Kinase 4/6. Cancer Res. 66, 7661-7667 (2006).
Testa, U., Castelli, G. & Pelosi, E. Lung Cancers: Molecular Characterization, Clonal Heterogeneity and Evolution, and Cancer Stem Cells. Cancers (Basel). 10, 248 (2018).
Eisenhauer EA, Therasse P, Bogaerts J, Schwartz LH, Sargent D, Ford R, et al. New response evaluation criteria in solid tumours: Revised RECIST guideline (version 1.1). Eur J Cancer. 2009;45:228-47. doi:10.1016/j.ejca.2008.10.026.
Conroy JM, Pabla S, Glenn ST, Burgher B, Nesline M, Papanicolau-Sengos A, et al. Analytical Validation of a Next-Generation Sequencing Assay to Monitor Immune Responses in Solid Tumors. J Mol Diagnostics. 2018; 20:95-109. doi:10.1016/j.jmoldx.2017.10.001.
Therneau TM, Lumley T. Survival Analysis Guide. Cran. 2017; 143.
Lê S, Josse J, Husson F. FactoMineR: An R Package for Multivariate Analysis. J. Stat Softw. 2008; 25:1-18. doi:10.18637/jss.v025.i01.
International Search Report and the Written Opinion of the International Searching Authority, International Application No. PCT/US2019/045962, pp. 1-15, dated Nov. 27, 2019.
International Preliminary Report on Patentability, International Application No. PCT/US2019/045962, pp. 1-8, dated Feb. 16, 2021.
Jan Budczies et al.: "Chromosome 9p copy number gains involving PD-L1 are associated with a specific proliferation and immune-modulating gene expression program active across major cancer types", BMC Medical Genomics, vol. 10, No. 1, Dec. 1, 2017 (Dec. 1, 2017), XP055642522, DOI: 10.1186/s12920-017-0308-8.

\* cited by examiner

Table 1 Patient characteristics

|  | Patients ($n = 120$) |
|---|---|
| Age at initial diagnosis (years) | |
| < 30 | 1 (00.0) |
| 30–39 | 1 (00.0) |
| 40–49 | 4 (03.3) |
| 50–59 | 28 (23.3) |
| 60–69 | 43 (35.8) |
| 70–79 | 34 (28.3) |
| ≥ 80 | 9 (07.5) |
| Mean | 65 |
| Sex | |
| Female | 61 (50.8) |
| Male | 59 (49.2) |
| Race | |
| White | 96 (80.0) |
| Other | 17 (14.2) |
| Unknown | 7 (05.8) |
| Vital status at last follow up | |
| Alive | 60 (50.0) |
| Dead | 60 (50.0) |
| Checkpoint inhibitor | |
| atezolizumab | 2 (01.7) |
| ipilimumab + nivolumab | 2 (01.7) |
| nivolumab | 79 (65.8) |
| pembrolizumab | 37 (30.8) |

FIG. 3

Table 2 Disease control for cell proliferation and PD-L1 IHC

| Cell Proliferation | PD-L1 IHC | DC | NDC | Total pts | DC rate | χ2 test |
|---|---|---|---|---|---|---|
| Moderately | | 22 | 22 | 44 | 50.0% | |
| Highly | | 9 | 33 | 42 | 21.4% | p = 0.0146 |
| Poorly | | 4 | 20 | 24 | 16.7% | p = 0.0113 |
| Poorly/highly | | 13 | 53 | 66 | 19.7% | p = 0.0017 |
| | Strongly positive (TPS ≥ 50%) | 16 | 16 | 32 | 50.0% | |
| | Not strongly positive (TPS < 50%) | 19 | 59 | 78 | 24.4% | p = 0.0009 |
| | Positive (TPS ≥ 1%) | 21 | 32 | 53 | 39.6% | |
| | Negative (TPS < 1%) | 14 | 43 | 57 | 24.6% | p = 0.1363 |
| Moderate | Strongly positive (TPS ≥ 50%) | 10 | 7 | 17 | 58.8% | |
| Poorly/highly | | 6 | 9 | 15 | 40.0% | p = 0.4786 |
| Moderately | Not strongly positive (TPS < 50%) | 12 | 15 | 27 | 44.4% | |
| Highly | | 4 | 25 | 29 | 13.8% | p = 0.0250 |
| Poorly | | 3 | 19 | 22 | 13.6% | p = 0.0438 |
| Poorly/highly | | 7 | 44 | 51 | 13.7% | p = 0.0063 |
| Moderately cold tumors (CD8 rank < 15%) | | 7 | 10 | 17 | 41.2% | |
| Poorly/highly cold tumors (CD8 rank < 15%) | | 7 | 33 | 40 | 17.5% | p = 0.1179 |
| Moderately cold tumors (CD8 rank < 33%) | | 5 | 5 | 10 | 50.0% | |
| Poorly/highly cold tumors (CD8 rank < 33%) | | 0 | 11 | 11 | 0.0% | p = 0.3298 |

FIG. 7

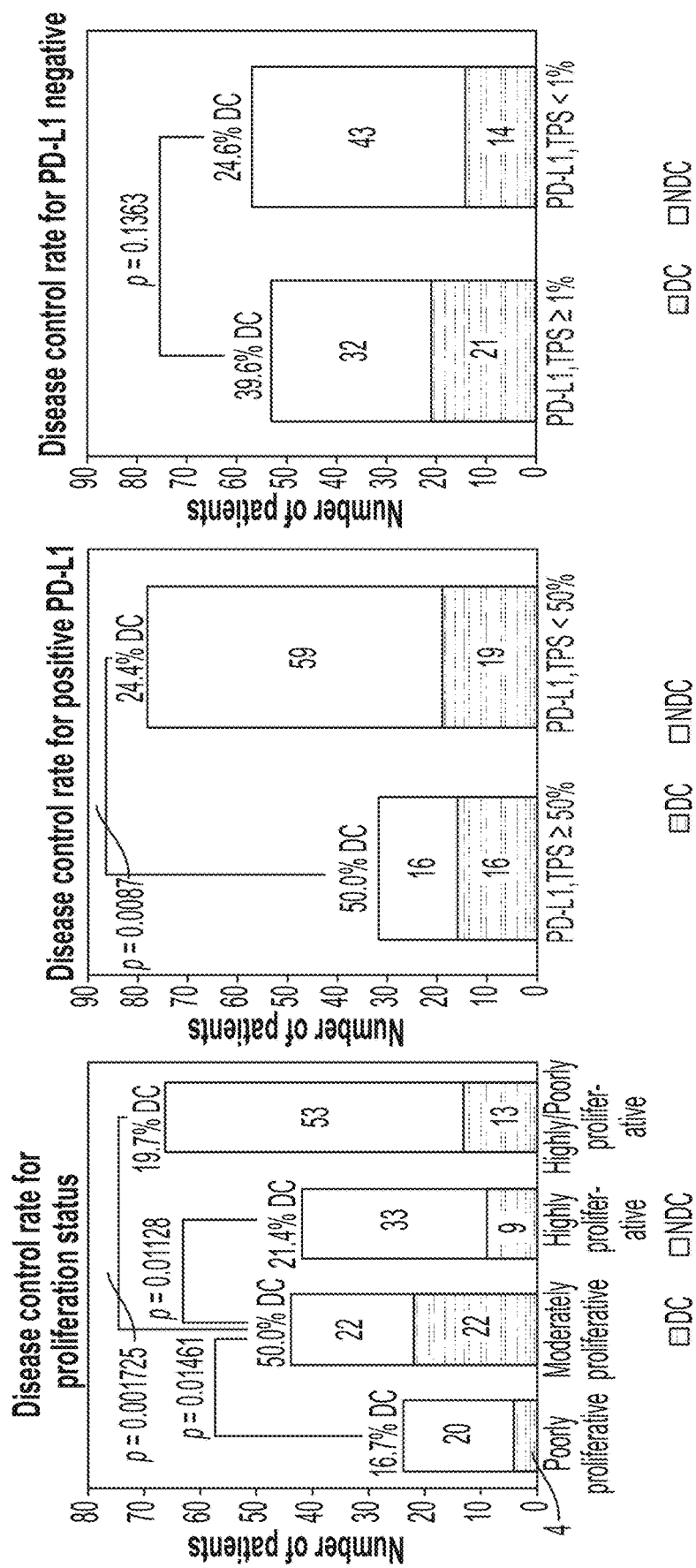

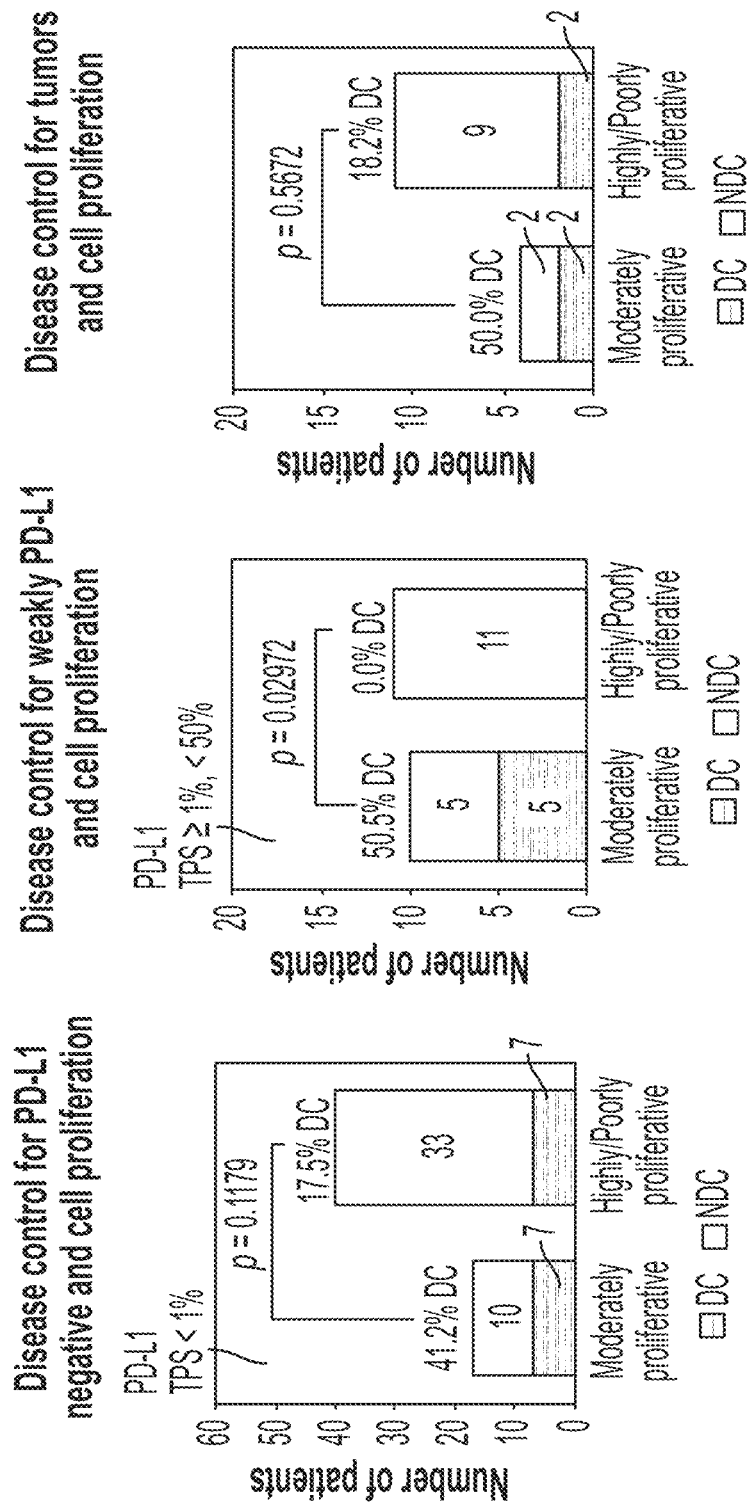

Table 3 Multivariate analysis

| Variable | Estimate | Std. Error | z value | p value |
|---|---|---|---|---|
| (Intercept) | 17.3526 | 2712.1561 | 0.006 | 0.9949 |
| Proliferation Moderately | 1.3503 | 0.5013 | 2.694 | 0.00707 |
| PD.L1. status Positive | 0.5169 | 0.547 | 0.945 | 034468 |
| Histology SCC.or.Other | -0.5898 | 0.6417 | -0.919 | 0.35801 |
| race Black or African American | -34.8319 | 3301.0002 | -0.011 | 0.99158 |
| race Black or African American | -16.7776 | 2712.156 | -0.006 | 0.99506 |
| race Other | -35.6219 | 4796.5772 | -0.007 | 0.99407 |
| race Other | -34.6736 | 4796.5771 | -0.007 | 0.99423 |
| race Unknown | -18.5693 | 2712.1561 | -0.007 | 0.99454 |
| race White | -17.9126 | 2712.1559 | -0.007 | 0.99473 |
| race White | -18.3781 | 2712.1559 | -0.007 | 0.99459 |
| sex M | 0.1522 | 0.5119 | 0.297 | 0.76616 |
| age_cat 1-29 | -35.0709 | 4796.5772 | -0.007 | 0.99417 |
| age_cat 40-49 | -1.201 | 1.6759 | -0.717 | 0.47359 |
| age_cat 50-59 | -0.6471 | 0.9129 | -0.709 | 0.47843 |
| age_cat 60-69 | -0.9142 | 0.8863 | -1.031 | 0.30233 |
| age_cat 70-79 | -1.1416 | 0.9098 | -1.255 | 0.20955 |

Analysis of deviance of each co-variate

| Co-variate | Df | Deviance | Resid. Df | Resid. Dev | P value(>Chi) |
|---|---|---|---|---|---|
| NULL | | | 109 | 137.61 | |
| Proliferation | 1 | 11.1163 | 108 | 126.49 | 0.0008557 |
| PD.L1. status | 1 | 4.5112 | 107 | 121.98 | 0.0336733 |
| Histology | 1 | 0.0593 | 106 | 121.92 | 0.8076295 |
| race | 7 | 7.4867 | 99 | 114.44 | 0.3800195 |
| sex | 1 | 0.1064 | 98 | 114.33 | 0.7442778 |
| age_cat | 5 | 4.2582 | 93 | 110.07 | 0.5128654 |

FIG. 9

| Cell Proliferation | PD-L1 IHC | OR | PD or SD | Total pts | DC rate | χ2 test |
|---|---|---|---|---|---|---|
| moderate | | 5 | 12 | 17 | 29.4% | |
| poorly | | 4 | 31 | 35 | 11.4% | p = 0.1078 |
| | positive (TPS ≥ 1%) | 4 | 8 | 12 | 33.3% | |
| | negative (TPS < 1%) | 6 | 38 | 44 | 13.6% | p = 0.1143 |
| | positive (CPS ≥ 1) | 6 | 18 | 24 | 25% | |
| | negative (CPS < 1) | 4 | 28 | 32 | 12.5% | p = 0.2268 |
| moderate | positive (TPS ≥ 1%) | 2 | 5 | 7 | 28.6% | |
| poorly | positive (TPS ≥ 1%) | 2 | 2 | 4 | 50.0% | p = 0.4773 |
| moderate | negative (TPS < 1%) | 3 | 7 | 10 | 30.0% | |
| poorly | negative (TPS < 1%) | 2 | 29 | 31 | 6.5% | p = 0.04784 |
| moderate | positive (CPS ≥ 1) | 3 | 7 | 10 | 30.0% | |
| poorly | positive (CPS ≥ 1) | 2 | 9 | 11 | 18.2% | p = 0.5254 |
| moderate | negative (CPS < 1) | 2 | 5 | 7 | 28.6% | |
| poorly | negative (CPS < 1) | 2 | 22 | 24 | 8.3% | p = 0.1599 |

FIG. 11

| Cell Proliferation | PD-L1 IHC | OR | PD or SD | Total pts | DC rate | χ2 test |
|---|---|---|---|---|---|---|
| moderately | | 5 | 12 | 17 | 29.4% | |
| poorly | | 4 | 31 | 35 | 11.4% | p = 0.1078 |
| | positive (TPS ≥ 1%) | 4 | 8 | 12 | 33.3% | |
| | negative (TPS < 1%) | 6 | 38 | 44 | 13.6% | p = 0.1143 |
| | positive (CPS ≥ 1) | 6 | 18 | 24 | 25% | |
| | negative (CPS < 1) | 4 | 28 | 32 | 12.5% | p = 0.2268 |
| moderate | positive (TPS ≥ 1%) | 2 | 5 | 7 | 28.6% | |
| poorly | | 2 | 2 | 4 | 50.0% | p = 0.4773 |
| moderately | negative (TPS < 1%) | 3 | 7 | 10 | 30.0% | |
| poorly | | 2 | 29 | 31 | 6.5% | p = 0.04784 |
| moderate | positive (CPS ≥ 1) | 3 | 7 | 10 | 30.0% | |
| poorly | | 2 | 9 | 11 | 18.2% | p = 0.5254 |
| moderately | negative (CPS < 1) | 2 | 5 | 7 | 28.6% | |
| poorly | | 2 | 22 | 24 | 8.3% | p = 0.1599 |

FIG. 14

| Table 3: Multivariate analysis for prediction of no objective response. | | | | |
|---|---|---|---|---|
| Variable | Estimate | Std. Error | z value | p-value |
| (Intercept) | -14.4193 | 2399.5465 | -0.006 | 1.00 |
| Moderately Proliferative | -0.28357 | 1.42382 | -0.199 | 0.84 |
| Poorly Proliferative | 0.49011 | 1.94147 | 0.252 | 0.80 |
| TPS Positive | 0.27982 | 1.41943 | 0.197 | 0.84 |
| CPS Positive | 0.09341 | 1.19393 | 0.078 | 0.94 |
| TPS Negative & Poorly Proliferative | -3.43474 | 1.97113 | -1.743 | 0.08 |
| Race: White | 0.70445 | 1.40338 | 0.502 | 0.62 |
| sexM | -0.41891 | 1.06372 | -0.394 | 0.69 |
| diagnosis_age: 40-49 | 14.25776 | 2399.5458 | 0.006 | 1.00 |
| diagnosis_age: 50-59 | 12.97483 | 2399.5457 | 0.005 | 1.00 |
| diagnosis_age: 60-69 | 15.04253 | 2399.5453 | 0.006 | 1.00 |
| diagnosis_age: 70-79 | 12.94012 | 2399.5457 | 0.005 | 1.00 |
| Analysis of deviance of each co-variate. | | | | |
| Co-variate | Df | Deviance | Residual Degrees of freedom | Residual deviation | p-value (>Chi) |
| NULL | | | 55 | 52.553 | |
| Proliferation | 2 | 2.5801 | 53 | 49.973 | 0.28 |
| PD.L1.status TPS | 1 | 1.0639 | 52 | 48.909 | 0.30 |
| PD.L1.status CPS | 1 | 0.0423 | 51 | 48.866 | 0.84 |
| ProliferationPoorly&PD.L1.status Nagative(TPS) | 1 | 3.4945 | 50 | 45.372 | 0.06 |
| race | 1 | 0.0818 | 49 | 45.29 | 0.77 |
| sex | 1 | 0.1513 | 48 | 45.139 | 0.70 |
| diagnosis_age | 4 | 2.998 | 44 | 42.141 | 0.56 |

FIG. 16

METHODS AND SYSTEMS FOR ASSESSING PROLIFERATIVE POTENTIAL AND RESISTANCE TO IMMUNE CHECKPOINT BLOCKADE

CROSS-REFERENCE TO RELATED APPLICATIONS

The present application claims priority to U.S. Provisional Application No. 62/717,379, filed on Aug. 10, 2018 and entitled "Methods and Systems for Assessing Proliferative Potential and Resistance to Immune Checkpoint Blockade, the entire contents of which are hereby incorporated by reference in its entirety.

FIELD OF THE INVENTION

The present disclosure is directed generally to methods and systems for characterizing tumor cell proliferation and resistance to immune checkpoint blockade therapy.

BACKGROUND

The U.S. Food and Drug Administration has approved several immune checkpoint inhibitors (ICI) for use in patients with one of several different types of cancer, including but not limited to Opdivo® from Bristol-Myers Squibb, Keytruda® from Merck, and Tecentriq® from Genentech. These drugs inhibit the interaction between the co-inhibitory receptor programmed cell death 1 (PDCD1, best known as PD-1) and its ligands—CD274 (best known as PD-L1) and programmed cell death 1 ligand 2 (PDCD1LG2, best known as PD-L2).

However, overall response rate (ORR) to these ICIs employed as standalone immunotherapeutic interventions is generally below 20%. Moreover, ICI-based immunotherapy has been estimated to cost USD 100,000-250,000 per patient, with some variation depending on specific ICI, treatment regimen and duration. Thus, considerable efforts are being devoted to the elucidation of the mechanisms whereby most tumors are refractory to ICIs, as well as to the identification of biomarkers with robust predictive value.

At least two main mechanisms of resistance to ICIs with direct clinical implications for cancer patients have been identified so far: (1) a reduced mutational burden, which limits the likelihood of malignant cells to be recognized by the immune system, and (2) the establishment of local immunosuppression via pathways that do not directly involve ICI targets such as PD-L1 and PD-1. These observations have rapidly been translated into the clinical management of some cancers such that determination of PD-L1 expression levels are approved by the U.S. FDA as a companion diagnostic for cancers such as lung cancer, and determination of tumor mutational burden (TMB) may follow soon.

However, response prediction based on TMB and/or PD-L1 levels is not sufficiently accurate. Indeed, it is known that a fraction of lung cancer patients responding to ICI-based chemotherapy have low-to-intermediate TMB and/or low PD-L1 expression. Conversely, not all patients with high TMB and/or high PD-L1 TPS obtain clinical benefits from ICIs, which suggests the existence of alternative resistance mechanisms, such as mutations that affect the ability of cancer cells to be recognized or eliminated by the immune system.

There are thousands of clinical trials evaluating ICI. Clinical trials commonly stratify patients based on gene marker analyses characterizing tumor response for eligibility for enrollment. Consequently, the method of characterizing tumor response to immune checkpoint blockade therapy is applied in both clinical settings for therapeutic selection as well as pre-clinical settings for clinical trials evaluating ICI.

SUMMARY OF THE INVENTION

There is a continued need in the art for more accurate and cost-effective prediction of tumor response to immune checkpoint blockade therapy, including prior to the initiation of an ICI.

The present disclosure is directed to a method for characterizing tumor response to immune checkpoint blockade therapy. Tissue from a tumor is analyzed to determine expression levels of one or more cell proliferation gene markers. The cell proliferation gene markers may include, for example, one or more of BUB1, CCNB2, CDK1, CDKN3, FOXM, KIAA0101, MAD2L1, MELK, MKI67, and TOP2A, among others. A proliferation profile of the tumor is determined based on the measured expression of the one or more cell proliferation gene markers, where the proliferation profile may be poorly proliferative, moderately proliferative, and highly proliferative categorizations. Similar or alternative proliferation profiles may be utilized. According to an embodiment, PD-L1 expression is measured from the tissue, and a PD-L1 profile for the tumor is determined, such as PD-L1 positive or PD-L1 negative. The proliferation profile, with or without the PD-L1 profile, is utilized to predict a response of the tumor to immune checkpoint blockade therapy. A physician can then determine, based on the predicted response of the tumor to immune checkpoint blockade therapy, a particular monotherapy or combination therapy for the tumor. Among many other improvements, the method therefore improves prediction of tumor response to immune checkpoint blockade therapy using cell proliferation, and improves stratification of patients for more precise and effective therapeutic decision-making.

According to an embodiment is provided a method for characterizing tumor response to immune checkpoint blockade therapy. The method includes: (i) obtaining tissue from the tumor; (ii) measuring, using the tissue, expression of one or more cell proliferation gene markers; (iii) determining, based on the measured expression of the one or more cell proliferation gene markers, a proliferation profile of the tumor; (iv) predicting, based on the determined proliferation profile, response of the tumor to immune checkpoint blockade therapy; and (v) determining, by a physician using the predicted response of the tumor to immune checkpoint blockade therapy, a monotherapy or combination therapy for the tumor.

According to an embodiment, the method further comprises: measuring, using the tissue, PD-L1 expression; and determining, based on the measured PD-L1 expression, a PD-L1 profile for the tumor, wherein the PD-L1 profile may be PD-L1 positive or PD-L1 negative; wherein the step of predicting response of the tumor to immune checkpoint blockade therapy is further based on the determined PD-L1 profile.

According to an embodiment, the expression of the one or more cell proliferation gene markers is measured by RNA-seq.

According to an embodiment, the one or more cell proliferation gene markers comprises one or more of BUB1, CCNB2, CDK1, CDKN3, FOXM1, KIAA0101, MAD2L1, MELK, MKI67, and TOP2A. According to an embodiment, the one or more cell proliferation gene markers comprises at least BUB1, CCNB2, CDK1, CDKN3, FOXM1, KIAA0101, MAD2L1, MELK, MKI67, and TOP2A.

According to an embodiment, the determined proliferation profile of the tumor comprises one or more of poorly proliferative, moderately proliferative, and highly proliferative.

According to an embodiment, the moderately proliferative proliferation profile is associated with a predicted more favorable response of the tumor to immune checkpoint blockade therapy.

According to an embodiment, the moderately proliferative proliferation profile is associated with a predicted more favorable response of the tumor to immune checkpoint blockade therapy, and wherein the poorly proliferative proliferation profile and the highly proliferative proliferation profile are associated with a predicted less favorable response of the tumor to immune checkpoint blockade therapy.

According to an embodiment, the method further comprises: measuring, using the tissue, PD-L1 expression; and determining, based on the measured PD-L1 expression, a PD-L1 profile for the tumor, wherein the PD-L1 profile may be PD-L1 positive or PD-L1 negative; wherein the step of predicting response of the tumor to immune checkpoint blockade therapy is further based on the determined PD-L1 profile, and wherein a tumor comprising a poorly proliferative proliferation profile and PD-L1 negative PD-L1 profile is associated with a predicted least favorable response of the tumor to immune checkpoint blockade therapy.

According to an embodiment, the determined therapy for the tumor is applied to the tumor. According to an embodiment, the determined therapy comprises immune checkpoint blockade therapy if the predicted response is favorable. According to an embodiment, the determined therapy comprises a therapy other than immune checkpoint blockade therapy if the predicted response is not favorable.

According to an embodiment is a method for treating a tumor. The method includes: (i) obtaining tissue from the tumor; (ii) measuring, using the tissue, expression of one or more cell proliferation gene markers, wherein the one or more cell proliferation gene markers comprises one or more of BUB1, CCNB2, CDK1, CDKN3, FOXM1, KIAA0101, MAD2L1, MELK, MKI67, and TOP2A; (iii) determining, based on the measured expression of the one or more cell proliferation gene markers, a proliferation profile of the tumor, wherein the determined proliferation profile of the tumor comprises one or more of poorly proliferative, moderately proliferative, and highly proliferative; (iv) measuring, using the tissue, PD-L1 expression; (v) determining, based on the measured PD-L1 expression, a PD-L1 profile for the tumor, wherein the PD-L1 profile may be PD-L1 positive or PD-L1 negative; (vi) predicting, based on the determined proliferation profile and the determined PD-L1 profile, response of the tumor to immune checkpoint blockade therapy; and (vii) determining, by a physician using the predicted response of the tumor to immune checkpoint blockade therapy, a monotherapy or combination therapy for the tumor, wherein the determined therapy comprises immune checkpoint blockade therapy if the predicted response is favorable, and wherein the determined therapy comprises a therapy other than immune checkpoint blockade therapy if the predicted response is not favorable; and (viii) applying the determined therapy to the tumor; wherein the moderately proliferative proliferation profile is associated with a predicted more favorable response of the tumor to immune checkpoint blockade therapy, and wherein the poorly proliferative proliferation profile and the highly proliferative proliferation profile are associated with a predicted less favorable response of the tumor to immune checkpoint blockade therapy.

According to an embodiment is an assay for characterizing tumor resistance to immune checkpoint blockade. The assay includes: (i) a measured expression of one or more cell proliferation gene markers obtained from tumor tissue; (ii) a determined proliferation profile of the tumor based on measured expression of one or more cell proliferation gene markers in the tumor tissue; (iii) a predicted response of the tumor to immune checkpoint blockade therapy based on the determined proliferation profile; and (iv) a therapy for the tumor determined by physician using the predicted response of the tumor to immune checkpoint blockade therapy.

According to an embodiment, the expression of the one or more cell proliferation gene markers is measured by RNA-seq.

According to an embodiment, the one or more cell proliferation gene markers comprises one or more of BUB1, CCNB2, CDK1, CDKN3, FOXM1, KIAA0101, MAD2L1, MELK, MKI67, and TOP2A. According to an embodiment, the one or more cell proliferation gene markers comprises at least BUB1, CCNB2, CDK1, CDKN3, FOXM1, KIAA0101, MAD2L1, MELK, MKI67, and TOP2A.

According to an embodiment, the assay further includes a determined PD-L1 profile for the tumor based on a measured PD-L1 expression in the tumor tissue, wherein the predicted response of the tumor to immune checkpoint blockade therapy is also based on the determined PD-L1 profile.

According to an embodiment, the determined proliferation profile of the tumor comprises one or more of poorly proliferative, moderately proliferative, and highly proliferative. According to an embodiment, the moderately proliferative proliferation profile is associated with a predicted more favorable response of the tumor to immune checkpoint blockade therapy. According to an embodiment, the moderately proliferative proliferation profile is associated with a predicted more favorable response of the tumor to immune checkpoint blockade therapy, and wherein the poorly proliferative proliferation profile and the highly proliferative proliferation profile are associated with a predicted less favorable response of the tumor to immune checkpoint blockade therapy.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely examples of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

BRIEF DESCRIPTION OF THE DRAWINGS

The present invention will be more fully understood and appreciated by reading the following Detailed Description in conjunction with the accompanying drawings, in which:

FIG. 3 is a table of patient characteristics, in accordance with an embodiment.

FIGS. 4A-4F are a series of charts showing results analyzing cell proliferation as an independent biomarker, in accordance with an embodiment, in which FIG. 4A shows the proportion of 120 NSCLC patients for cell proliferation by tertiles of poorly, moderately, and highly proliferative; FIG. 4B shows the proportion of 120 NSCLC patients positive or negative for PD-L1 IHC using a cut-off of tumor proportion score of ≥50% as a positive result; FIG. 4C shows the proportion of 120 NSCLC patients positive or negative for PD-L1 IHC using a cut-off of tumor proportion score of ≥1% as a positive result; FIG. 4D shows the prevalence for all combinations of strongly positive PD-L1 (TPS≥50%) cases and proliferation status; FIG. 4E shows the prevalence for all combinations of PD-L1 and proliferation status for weakly positive PD-L1 cases (TPS≥1 and <50%); and FIG. 4F shows the prevalence for all PD-L1.

FIGS. 6A-6D are a series of charts showing overall survival of 120 NSCLC patients receiving an immune checkpoint inhibitor (ICI) as part of their therapy, in accordance with an embodiment, in which: FIG. 6A is overall survival based upon stratification by cell proliferation for moderately versus combined poorly/highly proliferative; FIG. 6B is overall survival based upon stratification by cell proliferation for moderately versus poorly and highly proliferative; FIG. 6C is overall survival based upon stratification by PD-L1 expression levels using TPS≥50% as a cut-off for a positive result; and FIG. 6D is overall survival based upon stratification by strongly positive PD-L1 tumors and proliferation status (PD-L1 TPS≥50% moderately proliferative, PD-L1 TPS≥50% highly or poorly proliferative, PD-L1 TPS≥50% moderately proliferative, PD-L1 TPS≥50% highly or poorly proliferative).

FIG. 7 is a table showing disease control for cell proliferation and PD-L1 IHC, in accordance with an embodiment.

FIGS. 8A-8I are a series of charts showing the impact of PD-L1 levels and proliferative status on disease control rate in 110 NSCLC patients receiving an immune checkpoint inhibitor (ICI) as part of their therapy, in accordance with an embodiment, in which: FIG. 8A is the prevalence and DC rate for moderately versus highly and poorly proliferative tumors, as well as combined of the latter two; FIG. 8B is the prevalence and DC rate for strongly positive PD-L1 (TPS≥50%). FIG. 8C Prevalence and DC rate for PD-L1 negative (TPS<1%); FIG. 8D is the prevalence and DC rate for strongly positive PD-L1 combined with moderately versus highly/poorly proliferative tumors; FIG. 8E is the prevalence and DC rate for PD-L1 positive (TPS≥1%) combined with moderately versus highly/poorly proliferative tumors; FIG. 8F is the prevalence and DC rate for PD-L1 less than strongly positive (TPS<50%) combined with moderately versus highly/poorly proliferative tumors; FIG. 8G is the prevalence and DC rate for PD-L1 negative (TPS<1%) combined with moderately versus highly/poorly proliferative tumors; FIG. 8H is the prevalence and DC rate for weakly positive PD-L1 (TPS≥1% and <50%) combined with moderately versus highly/poorly proliferative tumors; and FIG. 8I is the prevalence and DC rate for minimal tumor infiltration by CD8+ T cells (so-called "cold" tumors) combined with moderately versus highly/poorly proliferative tumors.

FIG. 9 is a table showing a multivariate analysis of results, in accordance with an embodiment.

FIG. 11 is a table of patient characteristics, in accordance with an embodiment.

FIGS. 12A-12E are a series of graphs showing the prevalence of cell proliferation and PD-L1 expression, in accordance with an embodiment, in which: FIG. 12A shows the proportion of RCC patients for cell proliferation by tertiles of poorly, moderately, and highly proliferative; FIG. 12B shows the proportion of RCC patients for PD-L1 expression by IHC using a tumor proportion score (TPS) value of ≥1% as a positive result, or FIG. 12C a combined positive score (CPS) value of ≥1 as a positive result; FIG. 12D shows the proportion of PD-L1 TPS positive or negative RCC patients for tertiles of poorly, moderately, and highly proliferative; FIG. 12E shows the proportion of PD-L1 CPS positive or negative RCC patients for tertiles of poorly, moderately, and highly proliferative.

FIGS. 13A-13D are a series of graphs showing overall survival based upon PD-L1 IHC and cell proliferation status, in accordance with an embodiment, in which: FIG. 13A shows the overall survival upon stratification based on PD-L1 expression levels using TPS≥1% as a cut-off for a positive result, or FIG. 13B CPS≥1 as a cut-off for a positive result; FIG. 13C shows the overall survival of poorly versus moderately proliferative RCC patients; and FIG. 13D shows the overall survival of poorly versus moderately proliferative RCC patients for PD-L1 TPS negative and positive results.

FIG. 14 is a table showing proliferation and PD-L1 status is associated with best radiographic responses in patients treated with immune checkpoint blockade, in accordance with an embodiment.

FIGS. 15A-15D are a series of graphs showing objective response based upon PD-L1 IHC and cell proliferation status, in accordance with an embodiment, in which: FIG. 15A Objective response rate for PD-L1 expression by IHC using a tumor proportion score (TPS) value of ≥1% as a positive result, or FIG. 15B a combined positive score (CPS) value of ≥1 as a positive result. FIG. 15C Objective response rate for cell proliferation by tertiles of poorly, moderately, and highly proliferative, or FIG. 15D combined with PD-L1 TPS negative tumors.

FIG. 16 is table showing a multivariate analysis on all co-variates using a binomial logistic regression model, in accordance with an embodiment.

DETAILED DESCRIPTION OF EMBODIMENTS

The present disclosure is directed to method and systems for characterizing tumor response to immune checkpoint blockade therapy. In one embodiment, cell proliferation and resistance to immune checkpoint blockade were analyzed to demonstrate that high cellular proliferation in the tumor microenvironment is associated with resistance to ICI amongst cancer patients, and that the expression levels of gene sets associated with cellular proliferation can be harnessed to improve patient stratification based on tumor mutational burden (TMB) and/or PD-L1 tumor proportion score (TPS). In one embodiment, targeted RNA sequencing was employed to assess expression levels of several proliferation-related genes in diagnostic biopsies to provide improved information about cell proliferation and resistance to immune checkpoint blockade.

Figure 1:
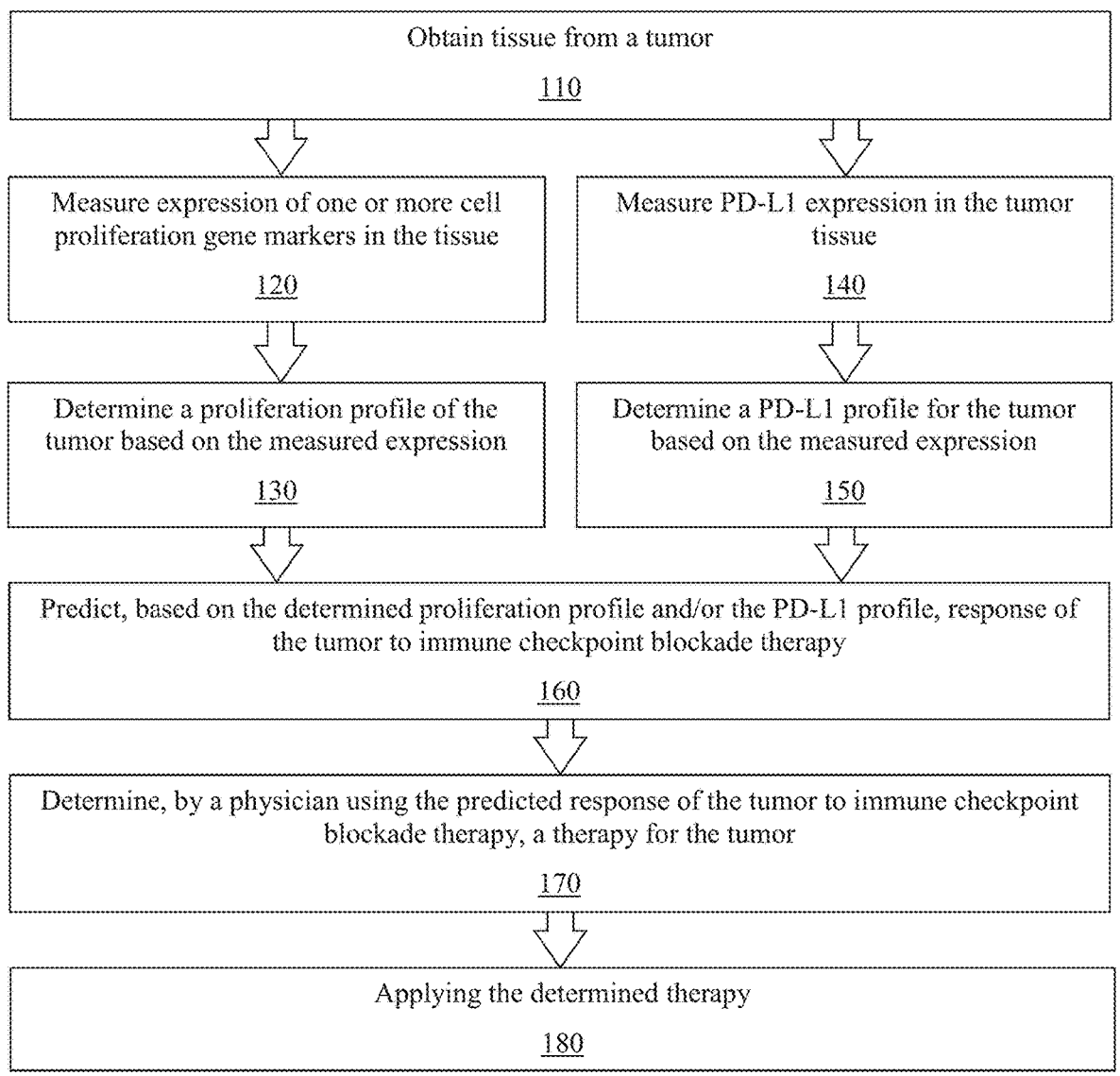
FIG. 1 is a flowchart of a method for characterizing tumor response to immune checkpoint blockade therapy, in accordance with an embodiment.

Referring to FIG. 1, in one embodiment, is a flowchart of a method 100 for characterizing tumor response to immune checkpoint blockade therapy. According to an embodiment, the method comprises a determination and application of a particular tumor therapy based on characterization of a tumor's response to immune checkpoint blockade therapy. The method may comprise any of the systems or embodiments described or otherwise envisioned herein.

At step 110 of the method, tissue is obtained from a patient's tumor for analysis. The patient may be any patient for which characterization of a tumor response to immune checkpoint blockade therapy is requested, desired, or prescribed. The tumor may be any tumor type for which characterization of a tumor response to immune checkpoint blockade therapy is requested, desired, or prescribed, and can include more than a single tumor. Some or all of the obtained tumor tissue may be obtained and immediately utilized for downstream analysis, and/or some or all of the obtained tumor tissue may be stored for a period of time before being utilized for downstream analysis. The tissue may be obtained from the tumor using any method for gathering tumor tissue. The amount of tissue obtained can be any amount, including amounts necessary for only the methods described herein as well as additional amounts for other analytical processes and/or storage.

At step 120 of the method, expression of one or more cell proliferation gene markers in the obtained tissue is analyzed. The expression of the one or more cell proliferation gene markers may be analyzed via global or targeted RNA-seq analysis of the tissue. Alternatively or additionally, the expression of the one or more cell proliferation gene markers may be analyzed by other methods. In addition to RNA sequencing (which includes targeted, mRNA and whole transcriptome modalities), other methods available to evaluate mRNA expression of cell proliferation include but are not limited to microarray analysis, reverse-transcription polymerase chain reaction (RT-PCR) including quantitative RT-PCR (qRT-PCR), Northern blots, serial analysis of gene expression (SAGE), digital droplet PCR (ddPCR), direct hybridization and fluorescent transcript counting and RNA fluorescent in situ hybridization (RNA-FISH), among others. Measurement of cell proliferation by protein expression includes immunohistochemistry (IHC), Western blots, fluorescent protein (FP) expression assays, immunoelectrophoresis, Mass Cytometry (CyTOF), fluorescence-based flow cytometry, Enzyme-linked immunosorbent assay (ELISA), and immunostaining techniques, among others.

The one or more cell proliferation gene markers may be any marker or markers that are suitable to determine a cell proliferation profile or status of the tissue. As just one non-limiting example, the one or more cell proliferation gene markers may be selected from among BUB1, CCNB2, CDK1, CDKN3, FOXM1, KIAA0101, MAD2L1, MELK, MKI67, and TOP2A. As another non-limiting example, the one or more cell proliferation gene markers may be all of the group consisting of BUB1, CCNB2, CDK1, CDKN3, FOXM, KIAA0101, MAD2L1, MELK, MKI67, and TOP2A alone or in combination with one or more additional genes. Many other candidates as described or otherwise envisioned herein are possible.

At step 130 of the method, a proliferation profile of the tumor is determined, selected, or characterized based on the measured expression of the one or more cell proliferation gene markers. The proliferation profile may be determined using any of a wide variety of methods. For example, the proliferation profile of the tumor may be determined by comparison of the expression level to predetermined threshold. As another example, the proliferation profile of the tumor may be determined by a machine learning algorithm that is trained with training data that associates expression levels and determined proliferation profiles.

A wide variety of proliferation profiles are possible. According to just one embodiment, the proliferation profile may comprise categories such as poorly proliferative, moderately proliferative, and highly proliferative, among others. Alternatively, the proliferation profile may be a specific number or other metric, a range, and/or any other method of quantifying proliferation.

At optional step 140 of the method, expression of PD-L1 in the obtained tissue is analyzed. The expression of PD-L1 may be determined by immunohistochemistry using known methodology. Alternatively or additionally, the expression of PD-L1 may be determined by other methods. In addition to immunohistochemistry approaches, the expression of PD-L1 may be determined by Western blots, fluorescent protein (FP) expression assays, immunoelectrophoresis, Mass Cytometry (CyTOF), fluorescence-based flow cytometry, Enzyme-linked immunosorbent assay (ELISA), and immunostaining techniques, among others. Alternatively or additionally, the expression of PD-L1 may be determined by methods such as RNA sequencing, microarray analysis, reverse-transcription polymerase chain reaction (RT-PCR) including quantitative RT-PCR (qRT-PCR), Northern blots, serial analysis of gene expression (SAGE), digital droplet PCR (ddPCR), direct hybridization and fluorescent transcript counting and RNA fluorescent in situ hybridization (RNA-FISH), among others.

At optional step 150 of the method, a PD-L1 profile for the tumor is determined, selected, or characterized based on the measured expression of PD-L1. The PD-L1 profile may be determined using any of a wide variety of methods. For example, the PD-L1 profile of the tumor may be determined by comparison of the expression level to predetermined threshold. As another example, the PD-L1 profile of the tumor may be determined by a machine learning algorithm that is trained with training data that associates expression levels and determined PD-L1 profiles.

A wide variety of PD-L1 profiles are possible. According to just one embodiment, the PD-L1 profile may comprise categories such as PD-L1 negative and PD-L1 positive, among others. Alternatively, the proliferation profile may be a specific number or other metric, a range, and/or any other method of quantifying proliferation.

At step 160 of the method, the response of the tumor to immune checkpoint blockade therapy is predicted based on the determined proliferation profile, with or without the determined PD-L1 profile. A wide variety of methods are possible for predicting the response of the tumor to immune checkpoint blockade therapy using the determined proliferation profile and/or the determined PD-L1 profile. For example, as just one non-limiting example, a moderately proliferative proliferation profile may be associated with a predicted more favorable response of the tumor to immune checkpoint blockade therapy, while a poorly proliferative proliferation profile and/or a highly proliferative proliferation profile may be associated with a predicted less favorable response of the tumor to immune checkpoint blockade therapy, although many other variations are possible. For example, a tumor comprising a poorly proliferative proliferation profile and PD-L1 negative PD-L1 profile may be associated with a predicted least favorable response of the tumor to immune checkpoint blockade therapy. Many other variations are possible, including different variations depending upon the tumor type. Accordingly, the method may comprise a lookup table, relationship calculator, and/or other methods or algorithms for associating the determined proliferation profile, with or without the determined PD-L1 profile, with a predicted response of the tumor to immune checkpoint blockade therapy.

According to an embodiment, the predicted response of the tumor to immune checkpoint blockade therapy is provided to a healthcare professional via a user interface, printout, report, and/or any other method of communicating the information. The report may comprise a detailed report, a single response prediction, analytical parameters, and/or other data.

At step 170 of the method, a physician utilizes the provided predicted response of the tumor to immune checkpoint blockade therapy, communicated by report or user interface, to determine a therapy for the tumor. For example, if the prediction indicates a poor response to immune checkpoint blockade therapy, the determined therapy may not include said therapy or may include one or more treatment methods in addition to immune checkpoint blockade therapy. As another example, if the prediction indicates a favorable response to immune checkpoint blockade therapy, the determined therapy may include immune checkpoint blockade therapy.

At step 180 of the method, the determined therapy is applied. The therapy may be applied using any method for treatment. According to an embodiment, applying the determined therapy may comprise ending and/or modifying a current therapy, among other options.

Figure 17:
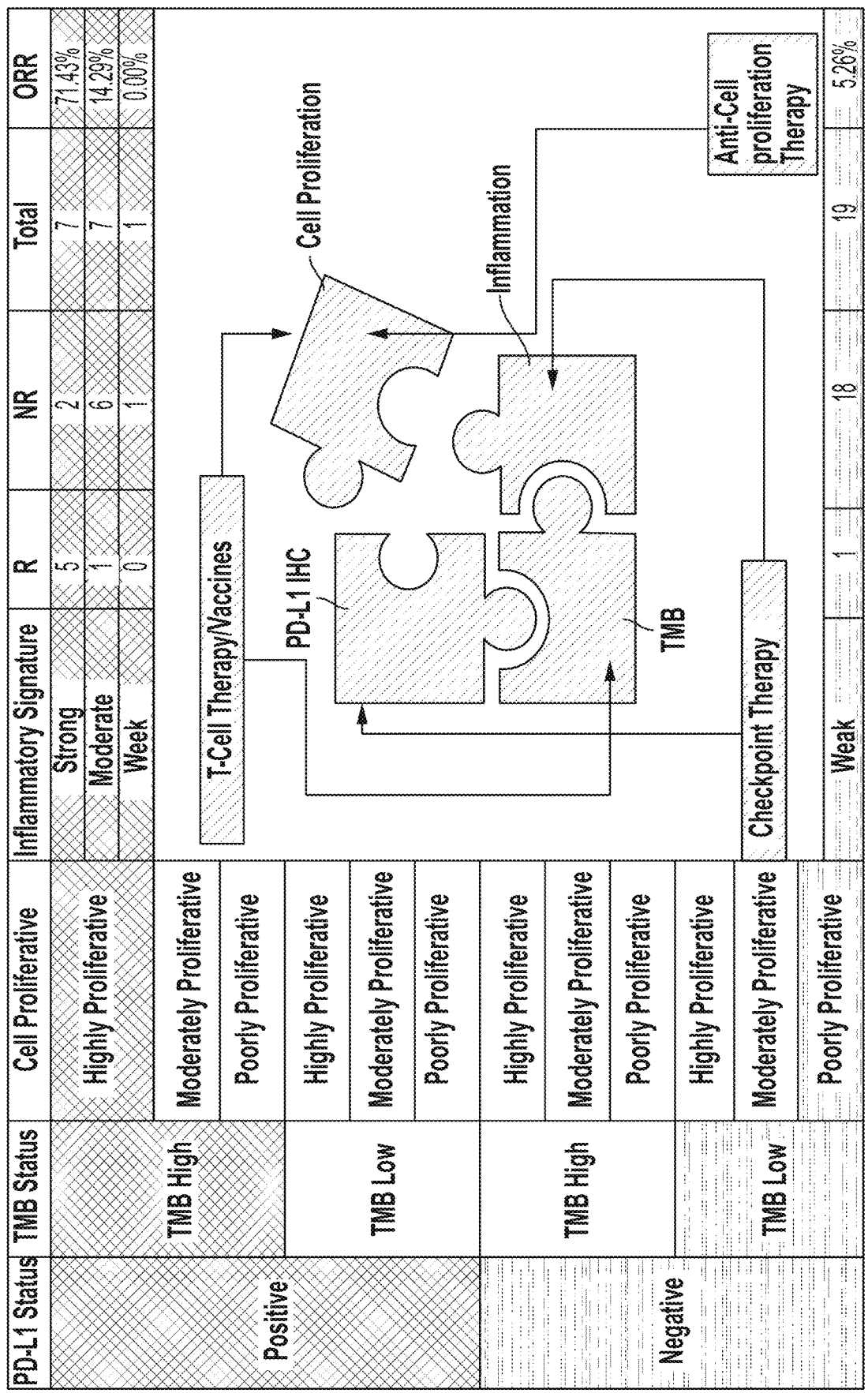
FIG. 17 is a chart showing the use of PD-L1, TMB, and/or cell proliferation for characterizing tumor response to immune checkpoint blockade therapy, in accordance with an embodiment.

Referring to FIG. 17, according to an embodiment, is one example showing use of PD-L1, TMB, and/or cell proliferation for characterizing tumor response to immune checkpoint blockade therapy.

Example 1—Lung Cancer Analysis

The following non-limiting example describes embodiments of a method for characterizing tumor response to immune checkpoint blockade therapy. Although non-limiting, the example demonstrates one approach using a characterized cell proliferation profile of a tumor to inform tumor treatment and therapy.

In this example, cell proliferation derived from the mean expression of 10 proliferation-associated genes (namely BUB1, CCNB2, CDK1, CDKN3, FOXM1, KIAA0101, MAD2L1, MELK, MKI67, and TOP2A), was identified as a marker of response to ICIs in NSCLC. Poorly, moderately, and highly proliferative tumors were somewhat equally represented in NSCLC, with tumors with the highest PD-L1 expression being more frequently moderately proliferative as compared to lesser levels of PD-L1 expression. Proliferation status had an impact on survival in patients with both PD-L1 positive and negative tumors. There was a significant survival advantage for moderately proliferative tumors compared to their combined highly/poorly counterparts ($p=0.021$). Moderately proliferative PD-L1 positive tumors had a median survival of 14.6 months that was almost twice that of PD-L1 negative highly/poorly proliferative at 7.6 months ($p=0.028$). Median survival in moderately proliferative PD-L1 negative tumors at 12.6 months was comparable to that of highly/poorly proliferative PD-L1 positive tumors at 11.5 months, but in both instances less than that of moderately proliferative PD-L1 positive tumors. Similar to survival, proliferation status has impact on disease control (DC) in patients with both PD-L1 positive and negative (DC) tumors. Patients with moderately versus those with poorly or highly proliferative tumors have a superior DC rate when combined with any classification schema used to score PD-L1 as a positive result (i.e., TPS≥50% or ≥1%), and best displayed by a DC rate for moderately proliferative tumors of no less than 40% for any classification of PD-L1 as a negative result. While there was an over representation of moderately proliferative tumors as PD-L1 expression increases this does not account for the improved survival or higher disease control rates seen in PD-L1 negative tumors.

Background

On Mar. 4, 2015, nivolumab (Opdivo®, from Bristol-Myers Squibb) became the first immune checkpoint inhibitor (ICI) to be approved by the US Food and Drug Administration for use in patients with metastatic nonsquamous non-small cell lung cancer (NSCLC) progressing on or after platinum-based chemotherapy, following disclosure of the results from the Phase III Checkmate-037 trial. Since then, three other ICIs that inhibit the programmed cell death pathway, including programmed cell death 1 (PDCD1 or CD279, best known as PD-1) and its ligands—CD274 (best known as PD-L1) and programmed cell death 1 ligand 2 (PDCD1LG2 or CD273, best known as PD-L2)—have been licensed for use in NSCLC patients, namely pembrolizumab (Keytruda® from Merck), atezolizumab (Tecentriq® from Genentech), and durvalumab (Imfinzi® from AstraZeneca).

However, response prediction based on PD-L1 levels is not 100% accurate. For instance, pembrolizumab monotherapy in NSCLC patients with a PD-L1 tumor proportion score (TPS)<1% (i.e., membranous PD-L1 expression on <1% malignant cells), of 1-49%, and ≥50% was associated with response rates of 10.7, 16.5, and 45.2%, respectively. Thus, a small population of NSCLC patients with low PD-L1, seemingly "negative bio-marker" patients, will still respond to ICI-based therapy. Conversely, not all patients with high PD-L1 TPS obtain clinical benefits from ICIs, which suggests the existence of alternative resistance mechanisms, such as mutations that affect the ability of cancer cells to be recognized or eliminated by the immune system, or other mechanism of local immunosuppression in the tumor microenvironment via pathways that do not directly involve ICI targets such as PD-L1 and PD-1.

Accordingly, the method described below employed targeted RNA sequencing of an immune related panel of slightly less than 400 genes to optimize the detection of low expressing genes as opposed to whole transcriptome, that was specifically designed for use in formalin fixed paraffin embedded (FFPE) clinical samples. This list of genes was divided into 41 different immune function categories and analyzed for response to ICIs in a cohort of NSCLC patients from ten different institutions. The highest association with response among the different immune function categories was cell proliferation, represented by the expression of ten unique genes. The approach demonstrates that either extreme of cellular proliferation in the tumor microenvironment, i.e. highly or poorly proliferative, is associated with resistance to ICIs amongst NSCLC patients, and that the expression levels of a 10-gene set associated with cellular proliferation can be harnessed to improve patient stratification beyond PD-L1 TPS. Most importantly, the approach described here shows that additional stratification of PD-L1 negative NSCLC based upon cell proliferation status introduces a new approach to response to ICI therapy in NSCLC.

Methods

Patients and Clinical Data.

Figures 2A, 2B:
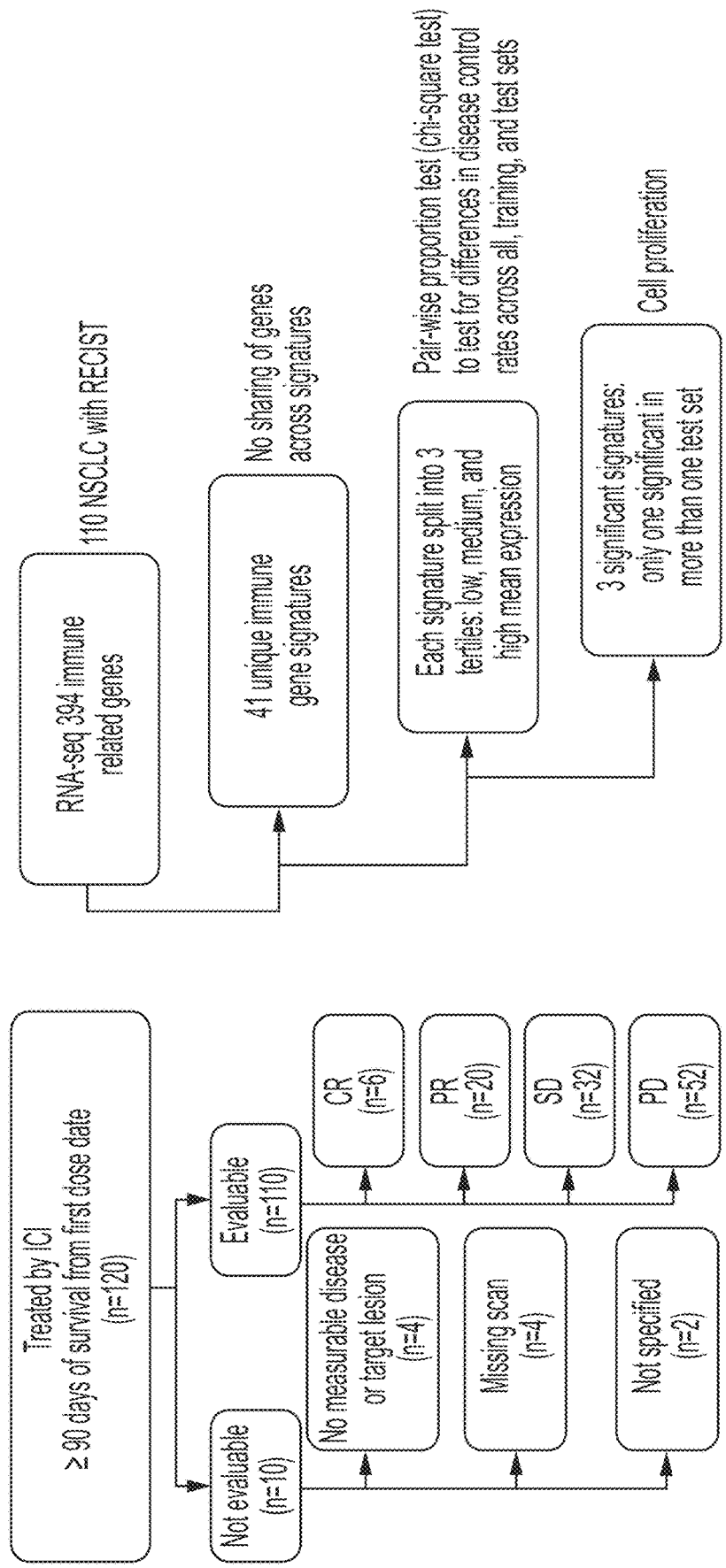
FIGS. 2A-2B are a flowchart summary of patient disposition and exploratory analysis, in accordance with an embodiment.

Ten collaborating institutions obtained approval by their respective institutional review boards to submit existing de-identified specimens and associated clinical data for use in this study. A total of 120 patients were included in the study as shown in FIGS. 2A and 2B, based on the following criteria: (1) history of Stage IV NSCLC; (2) availability of adequate archival formalin-fixed paraffin-embedded (FFPE) tissue collected prior to treatment with ICIs; (3) availability of sequencing data; and (4) availability of demographic, diagnosis, follow-up and survival data. The table in FIG. 3 summarizes the baseline clinical characteristics of these patients.

Patients who were treated with ICIs were included if they were treated by an agent approved by the FDA as of November 2017 and had follow up and survival from first ICI dose (n=120). ICI-treated patients who died within 90 days of first dose were excluded as it could not be discerned whether they were rapid progressors or had poor performance prior to going on drug. Patients lacking sufficient follow up time for response evaluation (less than 90 days from first dose), were also excluded from analysis. Of the 120 ICI-treated patients, for all of which survival data was available, there were 10 patients not evaluable for response due to either no measurable disease or target lesion (n=4), missing scans (n=4), or not specified (n=2) (FIG. 2A). For the remaining 110 patients all were evaluable for response based on RECIST v1.1 and were divided into a test set (n=34) from one institution with the most patients (Duke) and a training set (n=76) from all other institutions. Patients whose best response was complete response (CR), partial response (PR), or stable disease (SD) with 12 months or more survival were classified as disease control (DC), while patients whose best response was progressive disease (PD) or SD with less than 12 months survival were classified as no disease control (NDC). Duration of response was not available for all patients and not included for final analysis.

Immunohistochemical Studies.

The expression of PD-L1 on the surface of cancer cells was assessed in all cases by means of the Dako Omnis Platform and the 22C3 pharmDx antibody (Agilent, Santa Clara, Calif.) using FDA-scoring guidelines. Briefly, a minimum of 100 viable tumor cells were assessed for membranous staining of any intensity for the 22C3 antibody. The percentage of viable tumor cells showing partial or complete membrane staining relative to all viable tumor cells present in the sample (positive and negative) was then used to derive a tumor proportion score (TPS). PD-L1 levels were scored by a board-certified anatomic pathologist as per published guidelines, with a TPS≥50% considered as a strongly positive result for different comparisons, while a result of ≥1% considered as positive result for different comparisons. PD-L1 TPS≥1% to <50% were considered weakly positive for additional comparative purposes. PD-L1 TPS<1% was considered as negative. Ki-67 positivity amongst neoplastic and immune cells was scored upon nuclear staining, regardless of intensity, with the M7240 (clone MIB1) antibody from Dako (Carpentaria, Calif.) with the percentage of each cell type recorded.

RNA-Seq.

RNA were extracted from each sample and processed for targeted RNA-seq, as previously described. Gene expression was evaluated by amplicon sequencing of 394 immune transcripts on samples that met validated quality control (QC) thresholds.

Although targeted RNA sequencing was utilized, the method and systems described or otherwise envisioned herein are not limited to targeted RNA sequencing. In addition to RNA sequencing (which includes targeted, mRNA and whole transcriptome modalities), other methods available to evaluate mRNA expression of cell proliferation include but are not limited to microarray analysis, reverse-transcription polymerase chain reaction (RT-PCR) including quantitative RT-PCR (qRT-PCR), Northern blots, serial analysis of gene expression (SAGE), digital droplet PCR (ddPCR), direct hybridization and fluorescent transcript counting and RNA fluorescent in situ hybridization (RNA-FISH), among others. Measurement of cell proliferation by protein expression includes immunohistochemistry (IHC), Western blots, fluorescent protein (FP) expression assays, immunoelectrophoresis, Mass Cytometry (CyTOF), fluorescence-based flow cytometry, Enzyme-linked immunosorbent assay (ELISA), and immunostaining techniques, among others.

Data Analysis.

Immune gene expression ranks (range 0-100) from a targeted RNA-seq immune panel of approximately 400 genes were divided into 41 biological function categories according to commercial annotations from the manufacturer. For all 110 cases with response, distribution of each biological function was split into 3 tertiles of low (less than 33), medium (between 33 and 66) and high (greater than 66). A pair wise proportion test (chi-square test) was performed to test for difference in DC rates for these three tertiles (i.e. low vs medium, medium vs high and low vs high) for each biological function (FIG. 2B). Proportion test was performed with continuity correction and pair-wise p-values for each biological function were adjusted for multiple hypothesis testing using "holmes" correction.

The dataset was further divided into a training set (n=76) consisting of samples from all data access groups except the largest contributor. A separate test set (n=34) was constituted from samples from a single largest contributing institute. Any biological function that did not have cases representing one or more tertiles was removed from further analysis due to lack of dynamic range of that biological function in the population assessed in this study. The most significant gene functions were utilized for further analysis. Survival analysis was performed using a log-rank test on 5-year Kaplan-Meier survival curves for PD-L1 levels assessed by IHC and combined expression of 10 proliferation-related genes assessed by RNA-Seq. Comparison of DC rate was performed using Chi-square test with Yate's continuity correction. Multivariate analysis was performed by fitting a binomial logistic regression model to DC labels and co-variates such as proliferation status, PD-L1 status, histology, race, sex, and age category. Analysis of variance (ANOVA) was performed on the fitted model to study the table of deviance to determine the co-variate that explains the most variance in the DC rates.

Results

Immune-Related Gene Functions.

Among 41 different immune-related gene functions evaluated by pairwise comparison test in the training set (n=76), three were significantly differentially expressed for DC versus NDC for at least one comparison. These three functions and specific genes included proliferation [BUB1, CCNB2, CDK1, CDKN3, FOXM1, KIAA0101, MAD2L1, MELK, MKI67 (better known as Ki-67), and TOP2A;

maximum p=0.0092], antigen processing (CD74, HLA-A, HLA-B, HLA-C, HLA-DMA, HLA-DMB, HLA-DOA, HLA-DOB, HLA-DPA1, HLA-DPB1, HLA-DQA1, HLA-DQA2, HLA-DQB2, HLA-DRA, HLA-DRB1, HLA-E, HLA-F, HLA-F-AS1, HLA-G; p=0.0796), and dendritic cell (HERC6, IL3RA, ITGAX NRP1, TLR3, ZBTB46; p=0.0903). When both the training and test set (n=110) were used for the same comparison, proliferation was the only of these three functions that was significant, shown in FIG. 2B. Results for the test set (n=34) did not identify proliferation, antigen processing, or dendritic cell as significant, presumably due to the small size of the sample set. Proliferation was chosen for further evaluation based upon the identification as a significant factor in the training set as well as the combination of the training and test set.

Proliferative Status.

Figure 4C:
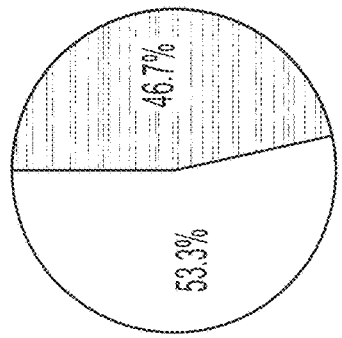
Figure 4B:
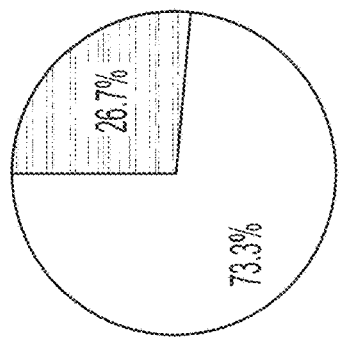
Figure 4A:
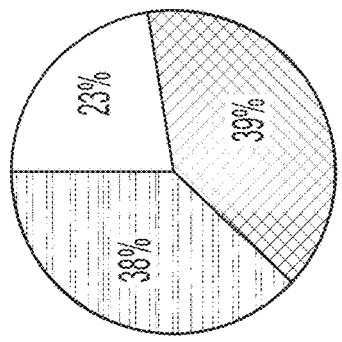

NSCLC had a wide distribution of poorly, moderately, and highly proliferative tumors with input by both neoplastic and immune cells that can be measured in more than one way. The mean expression rank values of 10 proliferation-related genes in 120 NSCLC specimens (adenocarcinoma n=94, sarcomatoid carcinoma n=1, squamous cell carcinoma n=25) was used as the primary indicator for the proliferative status of the tumor microenvironment. Tumors were stratified into poorly, moderately and highly proliferative based on the tertile rank of expression of this gene signature as compared to a separate reference population of 167 patients with multiple tumor types. Based on this analysis, poorly proliferative tumors were the least frequent in all available samples tested (27/120; 22.5%), followed by an equal distribution of highly (47/120; 39.2%) and moderately proliferative tumors (46/120; 38.3%), as shown in FIG. 4A.

Figure 5:
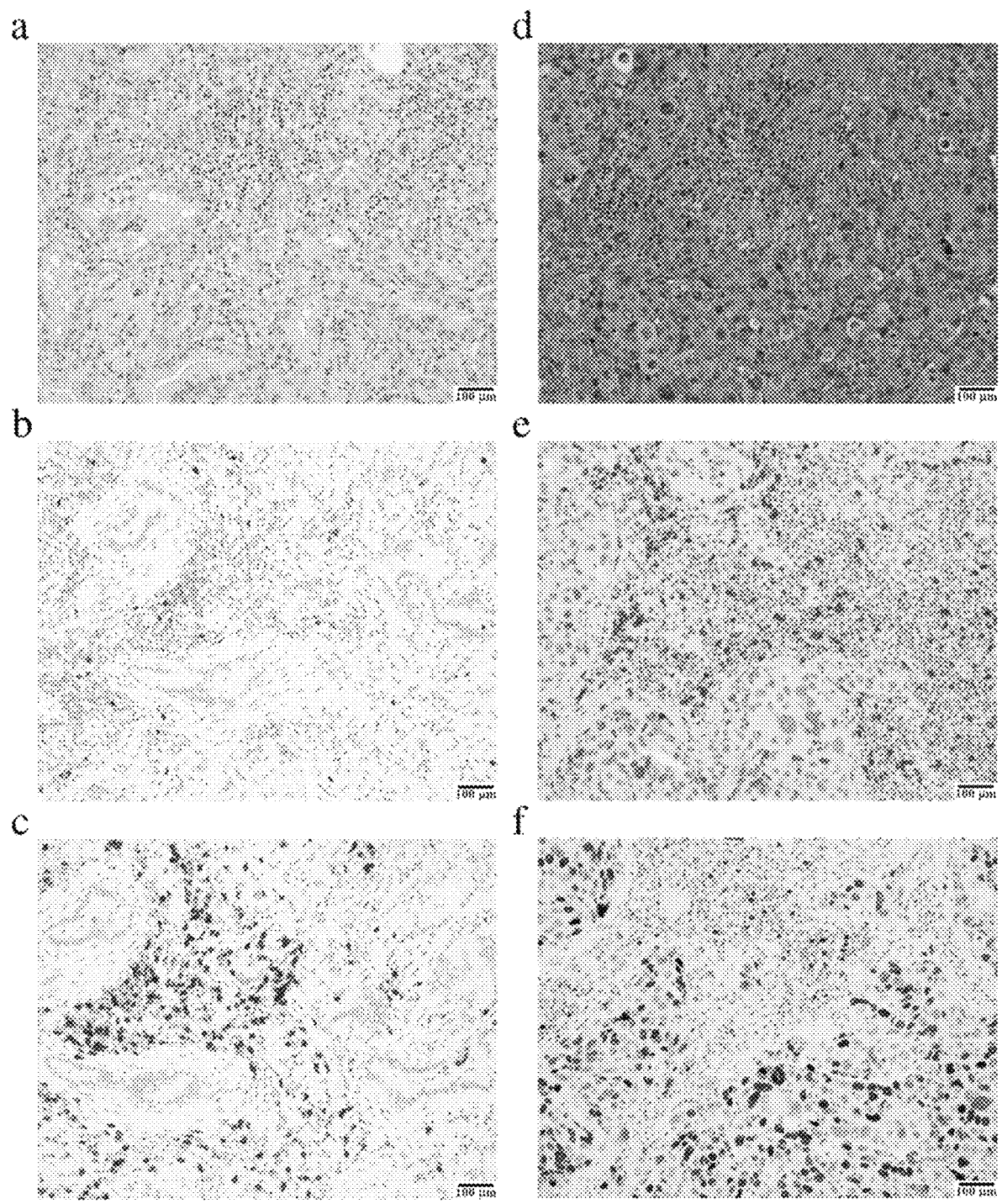
FIG. 5 is a series of images showing expression of MKI67 (Ki-67) in a variety of tumors, in accordance with an embodiment.

To define whether neoplastic cells, immune cells, or both constituted the source of proliferation-related transcripts, 7 highly proliferative and 9 poorly proliferative cases were evaluated by immunohistochemistry for the expression of MKI67 (best known as Ki-67), a biomarker of proliferation largely employed in the clinics. Highly proliferative tumors (as defined by RNA-seq) had >50% of neoplastic cells staining positive for Ki-67 in 6 out of 7 cases, while their poorly proliferative counterparts contained less than 40% Ki-67$^+$ neo-plastic cells in 8 of 9 cases. In a similar fashion, highly proliferative tumors had 5% or more of immune cells staining positive for Ki-67 in all cases, while their poorly proliferative counterparts showed only two cases with this degree of reactivity. Importantly, an abundant tumor CD8$^+$ T-cell infiltrate did not necessarily correlate with a highly proliferative tumor microenvironment. For example, in one poorly proliferative adenocarcinoma (FIG. 5a) there is a lack of staining by Ki-67 in both malignant and immune cells (FIG. 5b), even though there is an abundance of CD8$^+$ T cells (FIG. 5c). In comparison, for a highly proliferative adenocarcinoma (FIG. 5d) there is frequent staining by Ki-67 in both malignant and immune cells (FIG. 5e), with a similar number of CD8$^+$ T cells (FIG. 5f).

To evaluate the impact of single gene proliferation results, e.g. Ki-67, the mean expression rank values of all 10 proliferation-related genes were evaluated for accuracy (i.e. true positive plus true negatives divided by total number of results) for each gene individually. Accuracy ranged from a low of 52.7% for FOXM1 to a high of 67.3% for TOP2A, as compared to a value of 71.8% for the mean expression rank values of all ten proliferation-related genes. The accuracy of Ki-67 at 59.1% was near the mid-value of other single gene results.

The sum of all of these results suggest that poorly, moderately, and highly proliferative tumors are somewhat equally represented in NSCLC; that both immune cells and malignant cells are sources of proliferation-related transcripts, and it is possible to reach similar results for any of the 10 genes using only single gene evaluations.

Pd-L1 Expression.

Figures 4D, 4E, 4F:
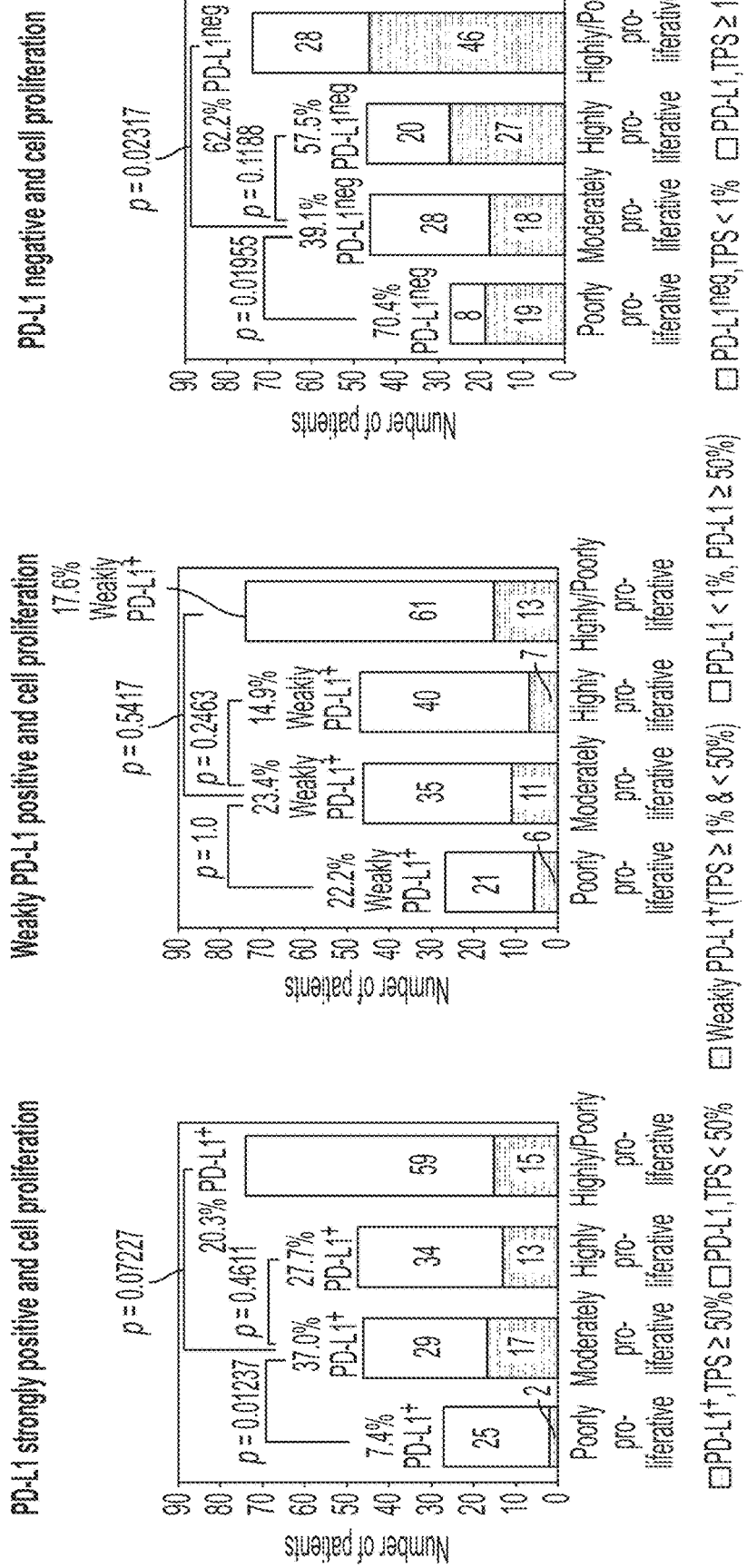

Tumors with the highest PD-L1 expression were more frequently moderately proliferative as compared to lower levels of PD-L1 expression. PD-L1 TPS, defined as the percentage of neoplastic cells displaying membranous positivity of any intensity upon staining with the DAKO 22C3 antibody, ranged from 0 to 100 and 32/120 (26.7%) of all cases were strongly positive (FIG. 4b), while 56/120 (46.7%) of all cases were positive at any level of staining (FIG. 4c). Moderately proliferative tumors were slightly enriched for strongly positive PD-L1 tumors as compared to highly proliferative tumors (p=0.4611), and more so as compared to poorly proliferative tumors (p=0.01237), or a combination of the latter two (p=0.07227), (FIG. 4d). For weakly positive PD-L1 tumors, moderately proliferative were not enriched as compared to poorly proliferative counterparts (p=1.0), highly proliferative (p=0.2463), or a combination of the latter two (p=0.5417), (FIG. 4e). For PD-L1 negative tumors, moderately proliferative were under represented as compared to poorly proliferative counterparts (p=0.01955), or a combination of poorly and highly proliferative (p=0.02317), but less so for highly proliferative (p=0.1188), (FIG. 4f). Overall these results support that as PD-L1 expression increases there is an over representation of moderately proliferative tumors, but as shown below does not account for the improved survival or higher disease control rates seen in PD-L1 negative tumors.

Overall Survival.

Figures 6A, 6B:
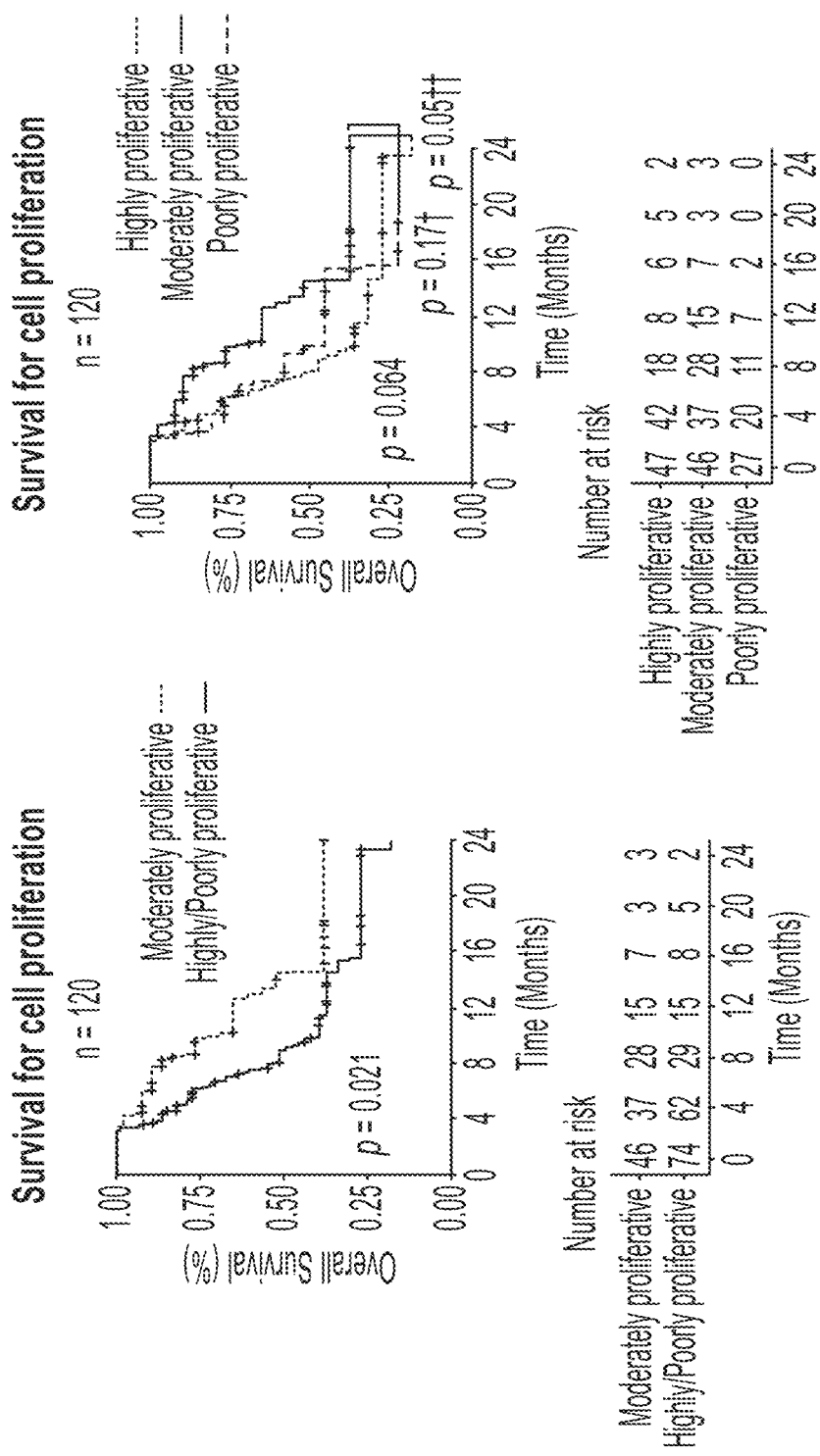
Figures 6C, 6D:
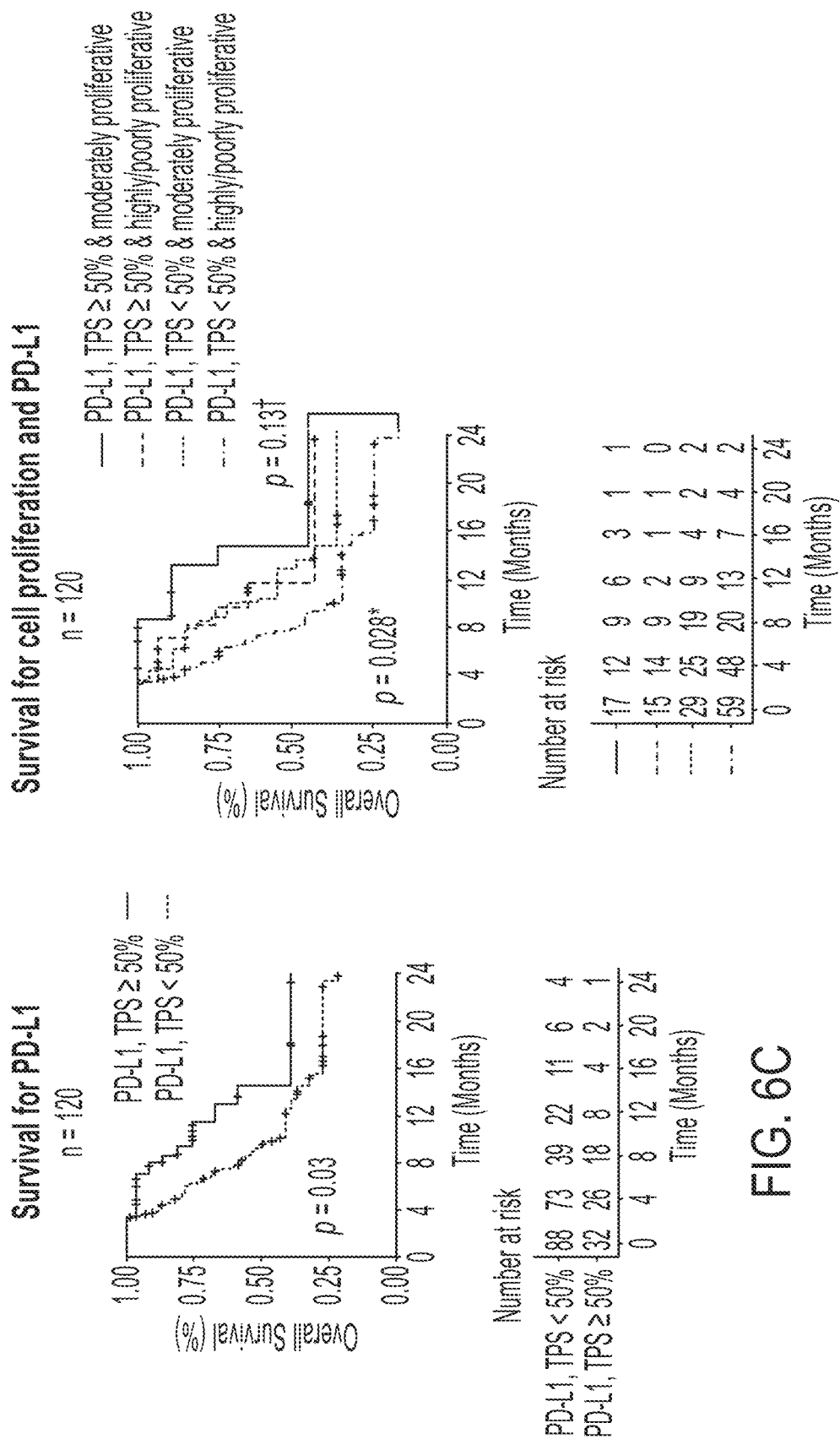
Figures 8D, 8E, 8F:
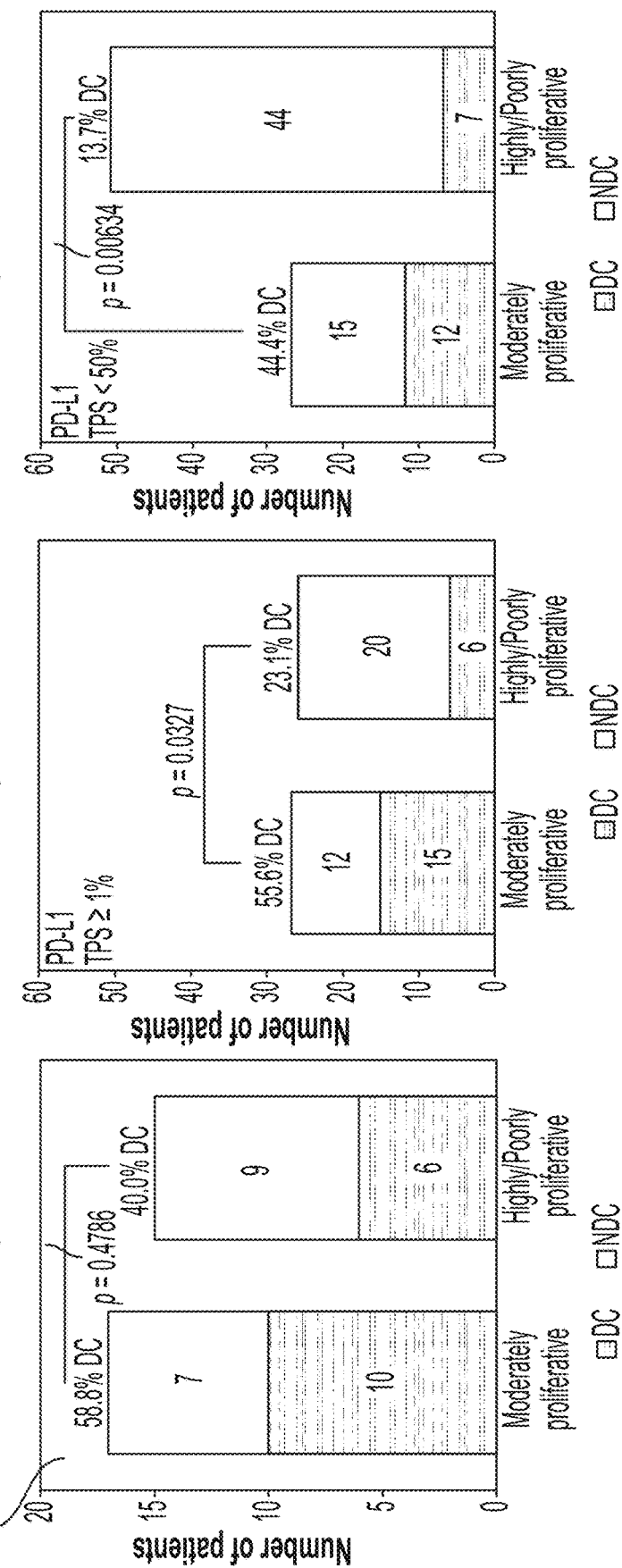

Proliferation status had an impact on survival in patients with both PD-L1 positive and negative tumors. There was a significant survival advantage for moderately proliferative tumors compared to their combined highly/poorly counterparts (p=0.021) (FIG. 6a). When highly and poorly proliferative groups were evaluated separately there was a trend towards survival for patients with moderately proliferative tumors (p=0.064) (FIG. 6b). Likewise, the survival of patients with strongly positive PD-L1 tumors was associated with a statistically significant survival advantage (p=0.03) (FIG. 6c). A combination of proliferation and PD-L1 resulted in a significant survival advantage in moderately proliferative strongly positive PD-L1 tumors with a median survival of 14.6 months that was almost twice that of all less than strongly positive PD-L1 highly/poorly proliferative tumors at 7.6 months (p=0.028) (FIG. 6d). Likewise, median survival in less than strongly positive PD-L1 moderately proliferative tumors at 12.6 months was comparable to that of highly/poorly proliferative strongly positive PD-L1 tumors at 11.5 months (p=0.86) (FIG. 6d), but in both instances less than that of moderately proliferative strongly positive PD-L1 tumors. The results for all PD-L1 positive tumors by a TPS≥1% criteria were very similar. The summary of these results support that moderately proliferative tumors have a survival advantage beyond PD-L1 positive tumors for NSCLC patients treated with checkpoint inhibitors.

Disease Control Rate.

Similar to survival, proliferation status had an impact on disease control in patients with both PD-L1 positive and negative tumors. The overall objective of evaluating disease control was to show this intersection of response to checkpoint inhibition for cell proliferation versus the current standard of PD-L1 IHC. The results, shown in the table in FIG. 7 and in FIGS. 8A-I, show that patients with moderately versus those with poorly or highly proliferative tumors have a superior DC rate when combined with any classification schema used to score PD-L1 as a positive result (i.e., TPS≥50% or ≥1%). The value of cell proliferation as a marker of response was best displayed by noting that the DC rate for moderately proliferative tumors was no less than 40% for any classification of PD-L1 as a negative result. This was critically important for the fifty-seven negative PD-L1 negative tumors for which moderately proliferative tumors had a DC rate of 41.2% (7/17) (FIG. 8g), while the DC rate among highly and poorly proliferative tumors combined was 17.5% (7/40, p=0.1179). The summary of all of these results support that cell proliferation is a relevant biomarker in all groups of NSCLC, but is unique and clinically useful for patients with PD-L1 negative tumors. Further support of this conclusion was a multivariate analysis on all co-variates using binomial logistic regression model showed that moderately proliferative tumors to have a significant association with probability of disease control (Table 3 in FIG. 9; p=0.0071). Furthermore, analysis of deviance of each co-variate (Table 3 in FIG. 9) suggests that adding proliferation to a null model improved it significantly (p=0.0009) followed by a second most informative co-variate of PD-L1 status (p=0.0337). Collectively these results suggest that, the proliferative status of the tumor microenvironment can be harnessed to improve patient stratification based on PD-L1 expression levels. Importantly, cell proliferation seems to have value as a biomarker of response in PD-L1 negative tumors.

Proliferative Status and Cold Tumors.

Proliferation status had an impact on disease control in patients with factors other than PD-L1 positive or negative status, impacting response to checkpoint inhibitors. In this regard, cell proliferation was further evaluated for value beyond PD-L1 status in the emerging recognition of inflammatory status, and more specifically the degree of CD8 infiltration. Response was evaluated for tumors with reduced levels of CD8-coding transcripts as compared to a reference population of 167 patients with multiple tumor types, which were previously demonstrated to indicate minimal tumor infiltration by $CD8^+$ T cells (so-called "cold" tumors). As there is currently no absolute criteria to define cold tumors, the method first arbitrarily defined this group by a CD8 rank less than 15, and then compared to those results to a non-arbitrary cut-off of the lower tertile of CD8 rank, or a value less than 33. Irrespective of the cut-off, DC was accurately predicted by the proliferative status of the tumor microenvironment (Table 2, although the numbers are quite small for the more stringent cut-off value (FIG. 8i). Most importantly, the DC rate was greater than 50% for any grouping of moderately proliferative cold tumors, while the rate was less than 20% for poorly/highly proliferative counterparts. PD-L1 status did not associate with response in cold tumors, again supporting that cell proliferation is a unique biomarker of response in NSCLC.

Discussion

The results show that a highly or poorly proliferative tumor microenvironment is associated with limited sensitivity to ICIs amongst NSCLC patients, and that targeted RNA-seq can be employed to assess the proliferative status of the tumor microenvironment at diagnosis, with the ultimate goal of improving clinical decision making based on PD-L1 only. Most importantly, these results show that some highly or poorly proliferative tumors may be resistant to ICIs independent of PD-L1 or inflamed status and that both PD-L1 positive and PD-L1 negative tumors at any TPS value can be stratified more accurately by cell proliferation. Moving forward, the need for standardization of cell proliferation may be vital in comparing response among various studies.

While the proliferative potential of malignant cells as assessed by Ki-67 positivity has been employed over the past 3 decades for prognostic purposes in a number of tumors, Ki-67 as measured by RNA-seq analysis was not the most accurate predictor of disease control as a single gene result, but rather was TOP2A.

Example 2—Renal Cancer Analysis

The following non-limiting example describes embodiments of a method for characterizing tumor response to immune checkpoint blockade therapy. Although non-limiting, the example demonstrates one approach using a characterized cell proliferation profile of a tumor to inform tumor treatment and therapy.

In this example, tumor specimens from 56 patients with mRCC who received nivolumab at seven institutions were evaluated for PD-L1 expression (immunohistochemistry), cell proliferation (targeted RNA-seq) and outcome. For the 56 patients treated with nivolumab as standard of care, there were 2 complete responses and 8 partial responses for a response rate of 17.9%. Dividing cell proliferation into tertiles, derived from the mean expression of 10 proliferation-associated genes in a reference set of tumors, poorly proliferative tumors (62.5%) were more common than their moderately (30.4%) or highly proliferative (8.9%) counterparts. Moderately proliferative tumors were enriched for PD-L1 positive (7/17, 41.2%), as compared to their poorly proliferative counterparts (11.4%, 4/35). Objective response for moderately proliferative (5/17, 29.4%) tumors was higher than that of their poorly (4/35, 11.4%) proliferative counterparts, but not statistically significant (p=0.11). When cell proliferation and negative PD-L1 tumor proportion scores were combined statistically significant results were achieved (p=0.048), showing that patients with poorly proliferative and PD-L1 negative tumors have a very low response rate (2/31, 6.5%) as compared to moderately proliferative PD-L1 negative tumors (3/10, 39 30%). Thus, it is shown again that cell proliferation has value in predicting response to immune checkpoint blockade therapy.

Background

Immune checkpoint inhibitors (ICIs) have revolutionized the treatment of metastatic renal cell carcinoma (mRCC). In 2015, nivolumab (Opdivo®) became the first programmed cell death 1 (PD-1, CD279, or PDCD1) inhibitor to be approved by the US Food and Drug Administration for use in patients with mRCC progressing after prior antiangiogenic therapy (sunitinib, pazopanib, or axitinib). This approval was based on the results of the Phase III Checkmate-025 trial, which randomized VEGF-refractory patients to either everolimus, an mTOR inhibitor, or nivolumab. In this study, both PD-L1 negative and PD-L1 positive patients benefited from nivolumab compared with everolimus; therefore, PD-L1 status was deemed not predictive for response. In 2018, the combination of nivolumab and ipilimumab (Yervoy®) was approved as first line therapy in intermediate or poor risk, previously untreated advanced renal cell carcinoma based upon the results of the Phase III Checkmate-214 trial that randomized patients with mRCC to either ipilimumab-nivolumab or sunitinib. In this study PD-L1 positive tumors constituted the majority of patients who achieved a CR (34/40; 85%), but still did not significantly distinguish responders from nonresponders in the overall population. In the on-going phase II trial KEYNOTE-427, evaluating pembrolizumab (Keytruda®, from Merck) as first-line treatment for advanced RCC, interim results reported at ASCO 2018 for 82 patients in cohort A (clear cell RCC) did show a higher objective response rate for patients whose tumor expressed PD-L1 on neoplastic or immune cells in a combined positive score (CPS)≥1.

While similar observations in NSCLC have led to the FDA companion diagnostic for pembrolizumab treatment using PD-L1 expression levels assessed by the PD-L1 22C3 pharmDx assay (from Agilent), in the management of patients with metastatic RCC, PD-L1 expression analysis has not demonstrated robust predictive clinical utility. Based upon the current evidence, PD-L1 IHC as a complementary biomarker for response to checkpoint inhibition in mRCC varies from no value for single agent nivolumab to less than 50% accuracy for pembrolizumab or combination therapy. A population of mRCC patients with negative PD-L1 expression, seemingly "negative biomarker" patients, will still respond to ICI-based therapy, while many of those with a positive result, seemingly "positive biomarker" patients, still do not respond.

The results described above, for example, show in non-small cell lung cancer (NSCLC) that the proliferation status of the tumor is an additional biomarker of response that enhances predictive utility compared to PD-L1 expression alone. A cell proliferation signature, derived from the mean expression of 10 proliferation-associated genes (namely BUB1, CCNB2, CDK1, CDKN3, FOXM1, KIAA0101, MAD2L1, MELK, MKI67, and TOP2A), improved survival predictions in patients with both PD-L1 positive and negative tumors. More specifically, there was a significant survival advantage for moderately proliferative tumors compared to their combined highly/poorly proliferative counterparts. Proliferation status also had impact on response in patients with both PD-L1 positive and negative tumors. Described below is shown the utility of adding proliferation status to PD-L1 in determining ICI responses in mRCC.

Methods

Patients and Clinical Data.

Figure 10:
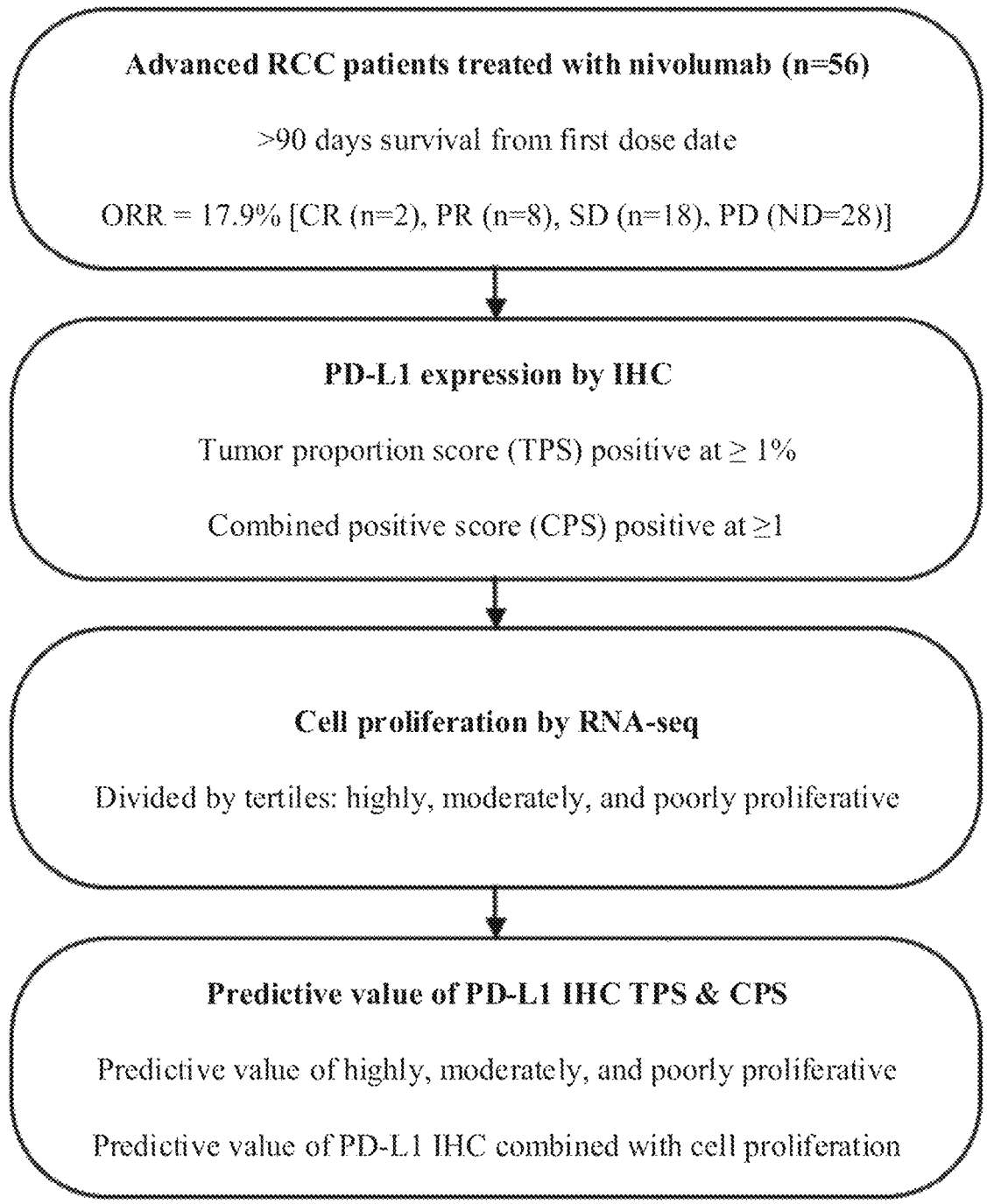
FIG. 10 is a flowchart showing information about patients included in the renal cancer study, in accordance with an embodiment.

Seven collaborating institutions obtained approval by their respective institutional review boards (IRBs) to submit existing de-identified specimens and associated clinical data for use in this study. A total of 56 patients were included in the study as shown in FIG. 10, based on the following criteria: (1) history of advanced RCC treated with ICI; (2) availability of adequate archival formalin-fixed paraffin-embedded (FFPE) tissue collected prior to treatment with nivolumab; (3) availability of sequencing data; and (4) availability of demographic, diagnosis, follow-up and survival data. Table 1 in FIG. 11 summarizes the baseline clinical characteristics of these patients.

Patients who were treated with nivolumab as approved by the FDA as of November 2015 and had follow up and survival from first dose (n=56) from 2015-2017 were included in this study. Patients who died within 90 days of first dose or who lacked sufficient follow up time for response evaluation (less than 90 days from first dose) were excluded from analysis. All patients were evaluated for response based on RECIST v1.1 criteria and were designated as complete response (CR), partial response (PR), stable disease (SD), and progressive disease (PD). CR and PR were included in the objective response rate. Duration of response was not available for all patients and not included for final analysis.

Immunohistochemical Studies.

The expression of PD-L1 on the surface of cancer cells was assessed in all cases using the Dako Omnis Platform and the 22C3 pharmDx antibody (Agilent, Santa Clara, Calif.). PD-L1 levels were scored by a board-certified anatomic pathologist as per published guidelines, with a tumor proportion score (TPS) in neoplastic cells of ≥1% considered positive. PD-L1 was also scored as combined positive score (CPS) evaluating both neoplastic and immune cells with a value of ≥1 considered positive, whereby the number of PD-L1 staining cells (tumor cells, lymphocytes, macrophages) divided by the total viable tumor cells is multiplied by 100.

RNA-Sequencing.

RNA were extracted from each sample and processed for targeted RNA-seq. Gene expression was evaluated by amplicon sequencing of 394 immune transcripts on samples that met validated quality control (QC) thresholds. From this list of genes were the previously described 10 genes related to cell proliferation that supported response prediction in NSCLC, and were utilized in this study to evaluate response in RCC.

Data Analysis.

Cell proliferation was evaluated for association with objective response and with PD-L1 IHC status as previously described herein. Briefly, the mean expression rank values of 10 proliferation-related genes [BUB1, CCNB2, CDK1, CDKN3, FOXM1, KIAA0101, MAD2L1, MELK, MKI67 (better known as Ki-67), and TOP2A] was used as an indicator for the proliferative status of the tumor microenvironment. Tumors were stratified into poorly, moderately, and highly proliferative based on an unbiased tertile rank of expression of this gene signature as compared to a separate reference population of 735 patients with multiple tumor types. Survival analysis was performed using a log-rank test on 5-year Kaplan-Meier survival curves for PD-L1 levels assessed by IHC and combined expression of 10 proliferation-related genes assessed by RNA-Seq. Comparison of objective response rate was performed using Chi-square test without Yate's continuity correction. Multivariate analysis was performed by fitting a binomial logistic regression model to objective response labels and co-variates such as proliferation status, PD-L1 status, histology, race, sex, and age category. Analysis of variance (ANOVA) was performed on the fitted model to study the table of deviance to determine the co-variate that explains the most variance in objective response rate.

Results

Patients.

Fifty-six nivolumab treated clear cell RCC patients were included (16 females, 40 males), with a median age of 59 (mean 59.3; range 37-79) at the time of diagnosis. There were 2 CR (3.6%), 8 PR (14.3%), 18 SD (32.1%), and 28 PD (50.0%), for an overall objective response rate of 17.9%. At the time of last follow-up (FU), 31 patients were alive (median FU 15.6 months, range 4.1-33.7 months) and 25 were deceased (median FU 11 months, range 3-31.2 118 months).

Proliferative Status.

Figures 12A, 12B, 12C:
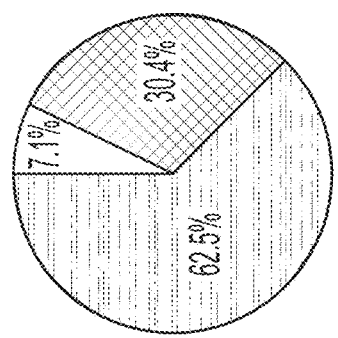

As compared to the prior results described above in NSCLC where poorly proliferative tumors were uncommon, in mRCC they were the most common group. Dividing cell proliferation into tertiles using the mean gene expression of 10 proliferation related genes as compared to a separate reference population of 735 patients with multiple tumor types, highly proliferative tumors were uncommon accounting for 7.1% (4/56). There were 30.4% moderately proliferative tumors (17/56), while the majority were poorly proliferative tumors (35/56; 62.5%). (FIG. 12a).

To evaluate the impact of single gene proliferation results, e.g. Ki-67, to the mean expression rank values of all 10 proliferation-related genes, accuracy was evaluated (i.e. true positive plus true negatives divided by total number of results) for each gene individually. Accuracy ranged from a low of 64.3% for MAD2L1 and Ki-67 to 75% for KIAA0101, as compared to accuracy of 69.6% for the mean expression rank values of all ten proliferation-related genes. Sensitivity, positive predictive value, and negative predictive value was highest for the mean expression rank values of all ten proliferation-related genes (50%, 29.4%, 87.2%, respectively). These results suggest that poorly proliferative tumors are much more common in RCC as compared to NSCLC, and it is possible to reach similar results for proliferative status using only single gene evaluations for any of the 10 genes evaluated.

PD-L1 Levels and Proliferative Status.

Figures 12D, 12E:
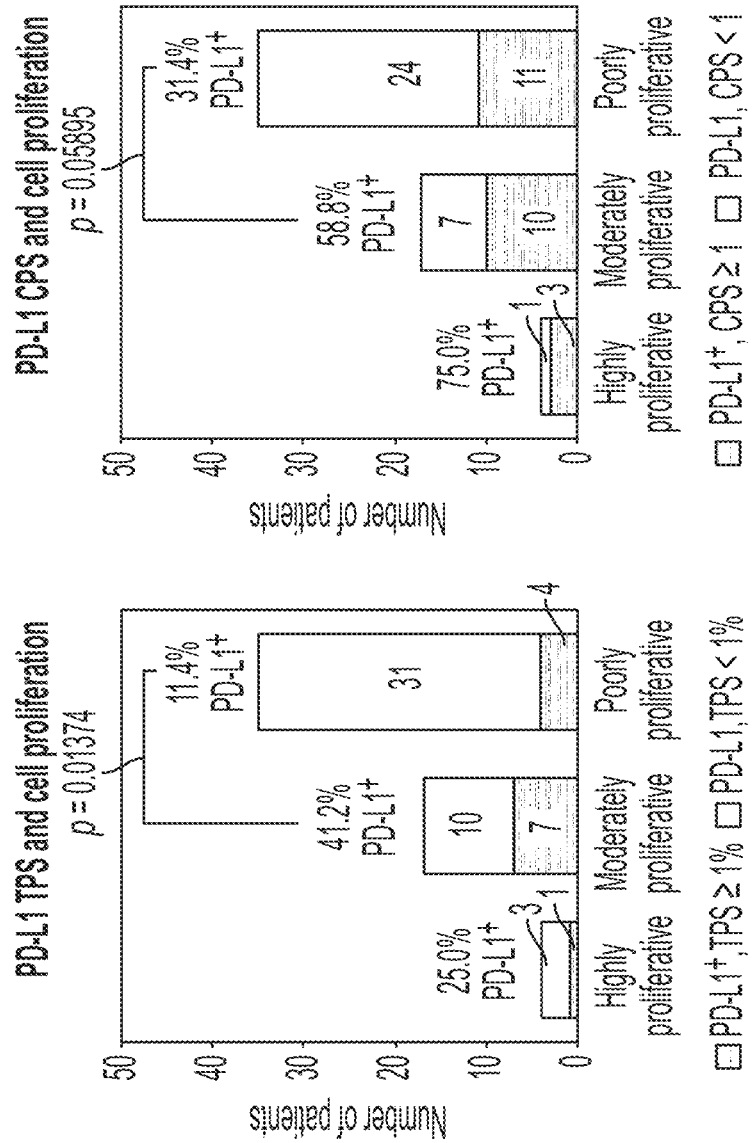

The rate of PD-L1 positive results in this study was very similar to prior clinical trials [2, 3, 5, 6], and tumors with positive PD-L1 expression were more frequently moderately proliferative as compared to poorly proliferative tumors. PD-L1 TPS status was positive in 21.4% (12/56), (FIG. 12b), while PD-L1 CPS was positive (CPS≥1) in 42.9% (24/56), (FIG. 12c). Moderately proliferative tumors had a statistically higher number of PD-L1 positive results (41.2%, 7/17), as compared to poorly proliferative tumors (11.4%, 4/35) by TPS scoring (p=0.014) (FIG. 12d), but not by CPS scoring (p=0.059) (FIG. 12e). While highly proliferative tumors showed frequent positive PD-L1 expression, their total numbers were too small for meaningful conclusions. Overall these results support that as PD-L1 expression and moderately proliferative tumors are correlated, and there may be an increase in frequency of PD-L1 expression in mRCC tumors as proliferation increases.

Overall Survival.

Figure 13A:
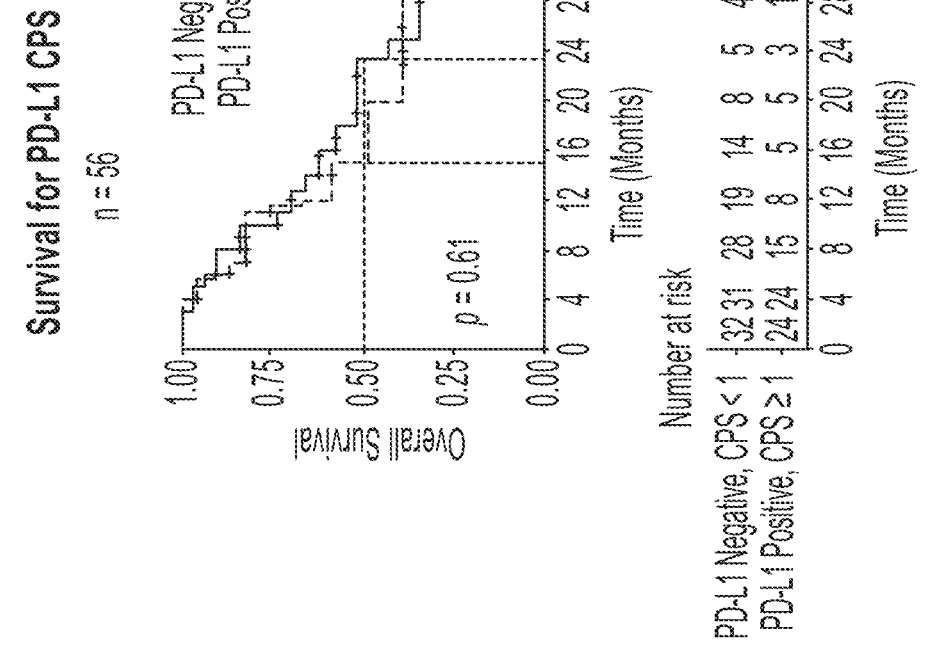
Figure 13B:
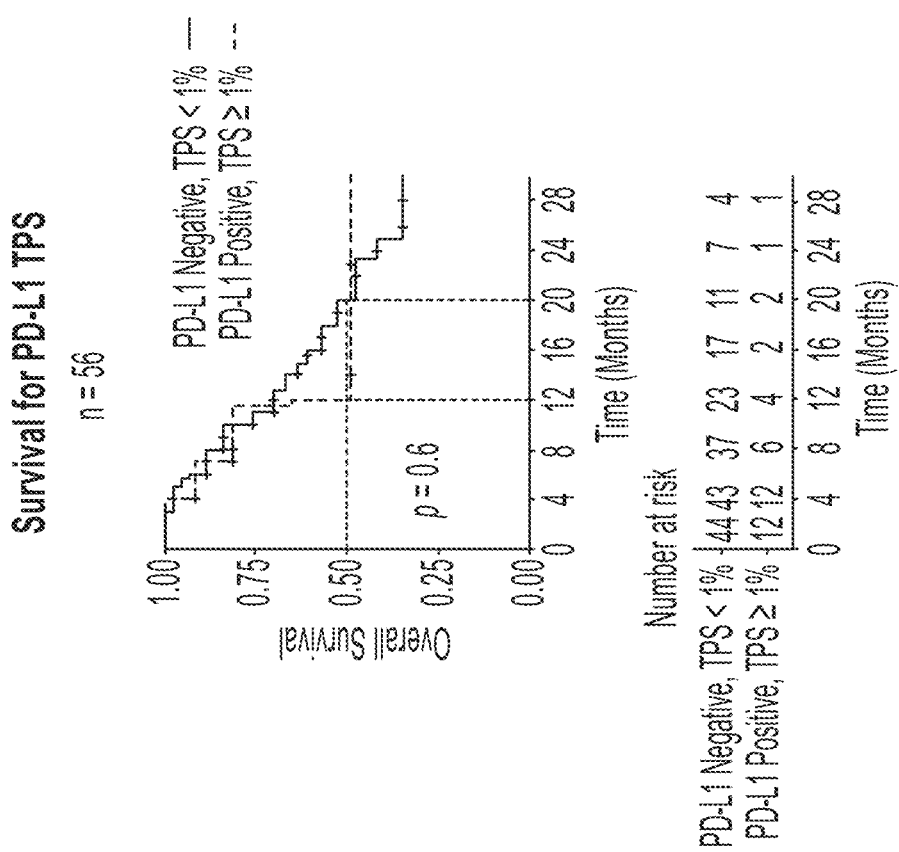
Figure 13D:
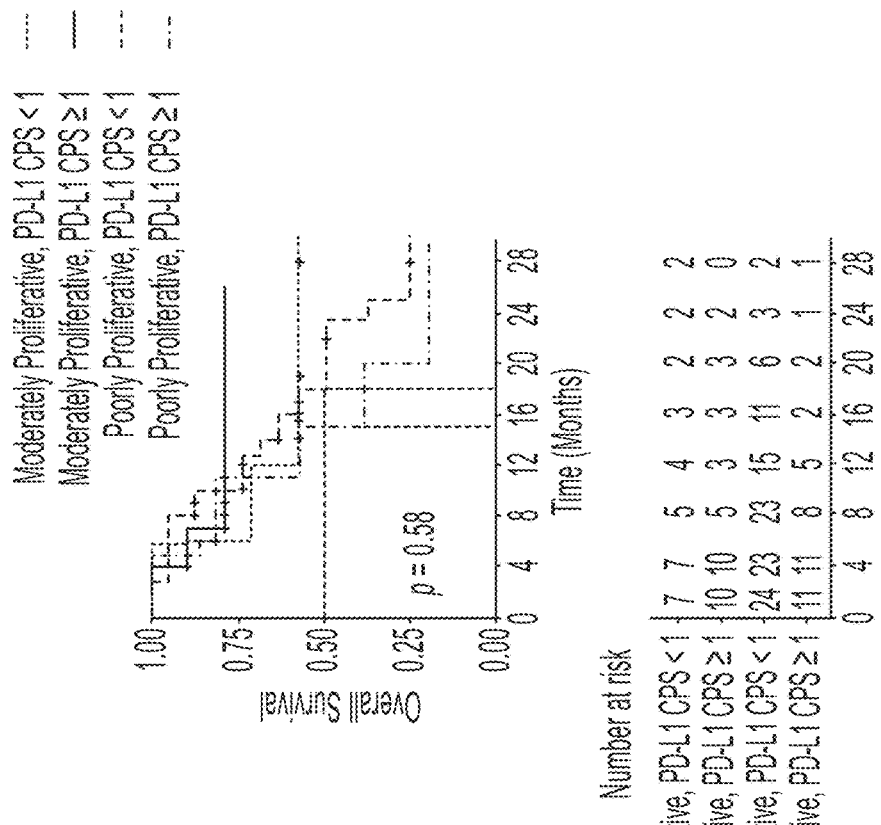
Figure 13C:
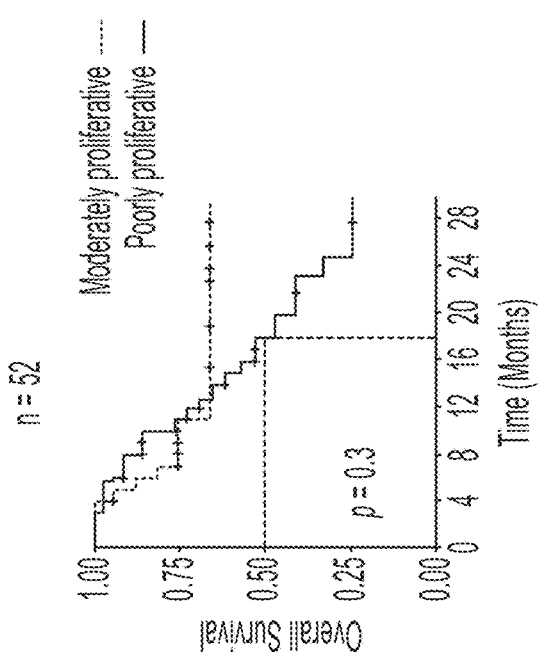

For the two proliferation groups with sufficient patients for analysis, median survival was not reached for moderately proliferative tumors compared to 18 months for poorly proliferative tumors (p=0.3) (FIG. 13c). In a comparable fashion, for PD-L1 expression median survival was reached for both groups by either method of analysis, i.e., TPS, (FIG. 13a), or CPS, (FIG. 13b), but was not statistically significant for PD-L1 positive tumors (p=0.6, p=0.61, respectively). Combining cell proliferation and PD-L1 status using CPS, whereby the number of PD-L1 positive versus negative were similar, no trend for survival advantage was noted (p=0.58) (FIG. 13d).

Objective Response.

Figure 15A:
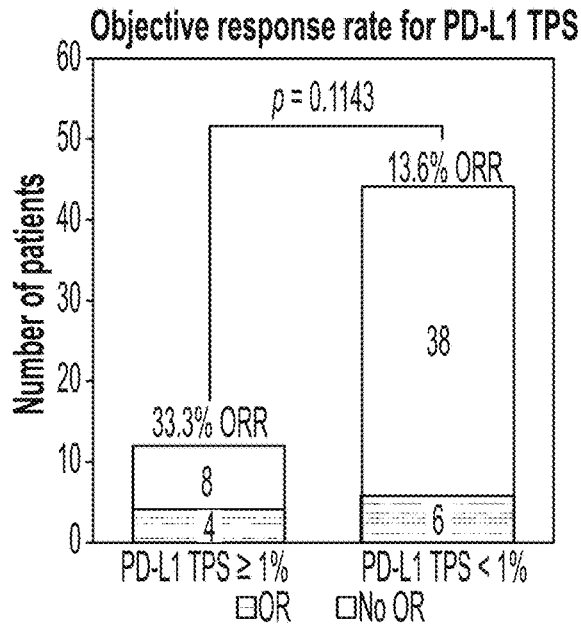
Figure 15B:
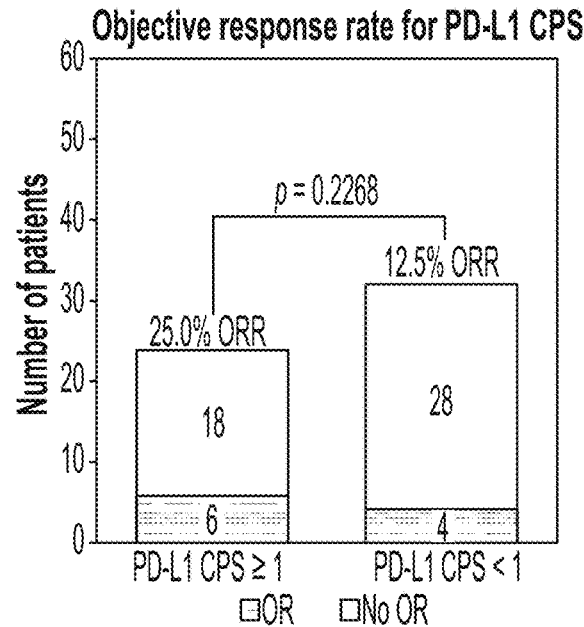
Figure 15C:
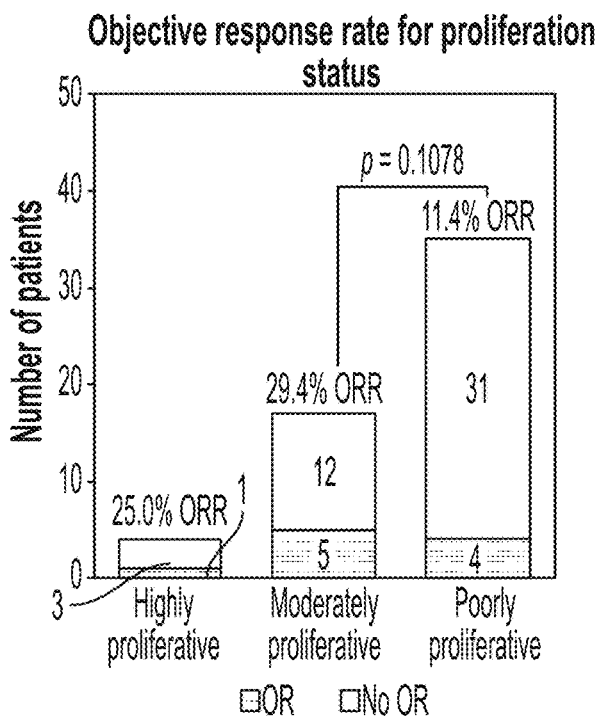
Figure 15D:
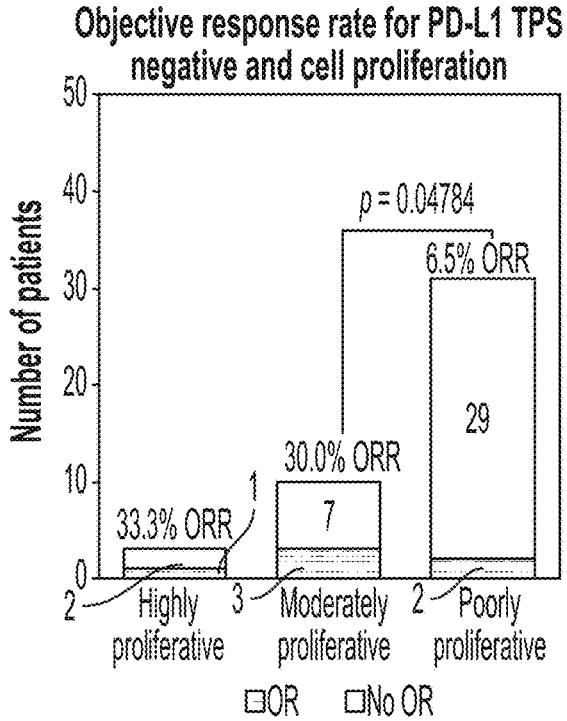

Proliferation and PD-L1 status was associated with best radiographic responses in patients treated with immune checkpoint blockade (objective response defined as complete or partial responses). The results, shown in FIGS. 15A-15D and the table in FIG. 14, show that patients with PD-L1 positive tumors have 2× or higher objective response rate for either TPS (positive 33.3%, 4/12; negative 13.6%, 6/44) or CPS (positive 25%, 6/24; negative 12.5%, 4/32) method of scoring, but statistical significance was not reached with either (p=0.114, p=0.227, respectively). Objective response for moderately proliferative (5/17, 29.4%) tumors was higher than that of their poorly (4/35, 11.4%) proliferative counterparts, but not statistically significant (p=0.108). Statistically significant results were achieved when cell proliferation and negative PD-L1 TPS were combined (p=0.048), showing that patients with poorly proliferative and PD-L1 negative tumors have a very low response rate (2/31, 6.5%) as compared to moderately proliferative PD-L1 negative tumors (3/10, 30%), (FIG. 15d). These results support that the combination of proliferative and PD-L1 status may constitute a predictive biomarker for the propensity of RCC patients to respond to ICIs. More specifically, these results support that cell proliferation has additive value in predicting lack of response in RCC patients with negative PD-L1 expression, which represents the majority of cases.

In further support of this conclusion, a multivariate analysis on all co-variates using a binomial logistic regression model showed that poorly proliferative tumors with no expression of PD-L1 in neoplastic cells had a significant association with lack of objective response (shown in Table 3 in FIG. 16; p<0.1). Furthermore, analysis of deviance of each co-variate (shown in Table 3 in FIG. 16) suggests that combining proliferation and PD-L1 expression in neoplastic cells to a null model improved response prediction significantly (p<0.1). Collectively these results suggest that the proliferative status of the tumor microenvironment may help further identify patients who will be unlikely to respond to single agent immune checkpoint blockade.

Discussion

The findings how that poorly proliferative clear cell RCC tumors with lack of expression of PD-L1 in neoplastic cells is associated with a very limited clinical response to nivolumab. The ultimate goal of targeted RNA-seq to assess the proliferative status of the tumor microenvironment is to improve clinical decision-making surrounding the use of checkpoint inhibitors beyond assessment of a single biomarker such as PD-L1 IHC, tumor mutational burden, PD-L1 amplification, recurrent genomic changes in RCC, or in many instances the use of no biomarker at all. A poorly proliferative, PD-L1 negative subset of RCC tumors encompassed the majority of cases in this study (n=32/56), and the response rate of 6.5% should warrant further investigation for alternative strategies for these patients, such as combination approaches. Oncologists have not routinely used PD-L1 IHC as a complementary diagnostic for nivolumab therapy in RCC due to lack of clinical utility in large phase 3 clinical trials similar to results for other tumor types.

The example shows the moderately proliferative tumors subset of RCC may be more sensitive to nivolumab, independent of tumor PD-L1 status, as both moderately proliferative, PD-L1 positive and moderately proliferative, PD-L1 negative tumors had similar rates of response, of approximately 30%. Highly proliferative tumors, as defined by an unbiased assessment of tertiles in comparison to a reference population of 735 tumors of 29 different tumor types, were quite uncommon in this study and were only briefly mentioned for this reason. In the above results of 120 NSCLC patients, highly and moderately proliferative tumors were equally common, while poorly proliferative were uncommon equally common, while poorly proliferative were uncommon in NSCLC. Differences between these studies were noted, as RCC tumors were noted to have a much lower overall rate of cell proliferation than NSCLC, but associations with response and survival were similar. In this example it is shown that RCC patients with poorly proliferative PD-L1 negative tumors have an extremely low rate of response to nivolumab, while patients with moderately proliferative, both PD-L1 positive and negative, constitute the majority of responders. A potential unifying concept for cell proliferation across various tumor types is that while the overall rate of proliferation is somewhat histology dependent, response is not. In other words, different tumor types will be noted for different proportions of poorly, moderately, and highly proliferative tumors, but moderate proliferation status trends toward an association with response to ICIs irrespective of this distribution of proliferation status. Certainly both of these studies suggest that cell proliferation can be used as a biomarker of response in PD-L1 negative tumors, independent of histology.

Cell proliferation, as assessed by Ki-67 positivity by IHC, has been studied in RCC. A recent meta-analysis of the peer-reviewed literature of over 4,000 RCC patients with Ki-67 positivity by IHC and survival data supports the generally accepted idea that a higher rate of Ki-67 is associated with poorer survival, distant metastases, and higher stage at presentation. However, in this and the results presented above, it is shown that cell proliferation as measured by the mean RNA-seq value of 10 proliferation related genes more accurately predicts response to ICIs than by single gene assessment.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A method for characterizing response of a patient's tumor to immune checkpoint blockade therapy, comprising:
   obtaining tissue from the tumor, wherein the tumor is non-small cell lung cancer (NSCLC) or renal cell carcinoma (RCC);
   measuring, using the tissue, expression of cell proliferation gene markers BUB1, CCNB2, CDKJ, CDKN3, FOXM1, KIA A0101, MAD2L1, MELK, MKI67, and TOP2A;
   determining, based on the measured expression of the cell proliferation gene markers, a proliferation profile of the tumor, wherein the determined proliferation profile of the tumor comprises moderately proliferative;
   predicting, based on the determined proliferation profile, response of the tumor to immune checkpoint blockade therapy, wherein the moderately proliferative proliferation profile is associated with a predicted favorable response of the tumor to immune checkpoint blockade therapy;
   determining, based on the predicted response of the tumor to immune checkpoint blockade therapy, an immune checkpoint blockade therapy for the tumor, wherein the immune checkpoint blockade therapy comprises one or more of nivolumab, pembrolizumab, ipilimumab, atezolizumab, and durvalumab; and
   administering the determined immune checkpoint blockade therapy to the patient.

2. The method of claim 1, wherein the expression of the cell proliferation gene markers is measured by RNA-seq.

3. A method for treating a tumor, comprising:
   obtaining tissue from the tumor, wherein the tumor is non-small cell lung cancer (NSCLC) or renal cell carcinoma (RCC);
   measuring, using the tissue, expression of a plurality of cell proliferation gene markers, wherein the plurality of cell proliferation gene markers comprises BUB1, CCNB2, CDK1, CDKN3, FOXM1, KIAA0101, MAD2L1, MELK, MKI67, and TOP2A;
   determining, based on the measured expression of the cell proliferation gene markers, a proliferation profile of the tumor, wherein the determined proliferation profile of the tumor comprises moderately proliferative;
   measuring, using the tissue, PD-L1 expression;
   determining, based on the measured PD-L1 expression, a PD-L1 profile for the tumor, wherein the PD-L1 profile may be PD-L1 positive or PD-L1 negative;
   predicting, based on the determined proliferation profile and the determined PD-L1 profile, response of the tumor to immune checkpoint blockade therapy, wherein the moderately proliferative proliferation profile is associated with a predicted favorable response of the tumor to immune checkpoint blockade therapy;
   determining, using the predicted response of the tumor to immune checkpoint blockade therapy, a therapy for the tumor, wherein the determined therapy comprises immune checkpoint blockade therapy; and
   administering a determined immune checkpoint blockade therapy to the tumor for which the predicted response is favorable, wherein the immune checkpoint blockade therapy comprises one or more of nivolumab, pembrolizumab, ipilimumab, atezolizumab, and durvalumab.

* * * * *